(12) United States Patent
Chen et al.

(10) Patent No.: US 12,048,432 B2
(45) Date of Patent: Jul. 30, 2024

(54) ROTATING MECHANISM AND SURGICAL STAPLER

(71) Applicant: Touchstone International Medical Science Co., Ltd., Suzhou (CN)

(72) Inventors: Zhi Chen, Suzhou (CN); Xiangjin Du, Suzhou (CN)

(73) Assignee: Touchstone International Medical Science Co., Ltd., Suzhou (CN)

( * ) Notice: Subject to any disclaimer, the term of this patent is extended or adjusted under 35 U.S.C. 154(b) by 240 days.

(21) Appl. No.: 17/756,394

(22) PCT Filed: Nov. 12, 2020

(86) PCT No.: PCT/CN2020/128287
§ 371 (c)(1),
(2) Date: May 24, 2022

(87) PCT Pub. No.: WO2021/104026
PCT Pub. Date: Jun. 3, 2021

(65) Prior Publication Data
US 2023/0000493 A1 Jan. 5, 2023

(30) Foreign Application Priority Data

Nov. 28, 2019 (CN) .......................... 201911195242.X
Nov. 28, 2019 (CN) .......................... 201922094449.X
Apr. 13, 2020 (CN) .......................... 202020538343.X

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/07207* (2013.01); *A61B 2017/00477* (2013.01);
(Continued)

(58) Field of Classification Search
CPC .............. A61B 17/068; A61B 17/072; A61B 17/07207; A61B 17/00234; A61B 17/115;
(Continued)

(56) References Cited

U.S. PATENT DOCUMENTS 3,525,272 A * 8/1970 Olson ...................... G05G 5/06
74/528
5,823,066 A 10/1998 Huitema et al.
(Continued)

FOREIGN PATENT DOCUMENTS

CN 203841747 U 9/2014
CN 104382627 A 3/2015
(Continued)

OTHER PUBLICATIONS

Extended European Search Report issued on Dec. 8, 2022 for European Patent Application No. 20894502.2 (12 pages).
(Continued)

*Primary Examiner* — Scott A Smith
(74) *Attorney, Agent, or Firm* — Fox Rothschild LLP

(57) ABSTRACT

A swing head mechanism and a medical stapler. The swing head mechanism comprises a rotating component, a swing head pull rod (93), and a housing. At least one first fitting member and at least one second fitting member are respectively provided on the outside of the rotating component and the inside of the housing. When the rotating component rotates relative to the housing until the first fitting member is opposite to the second fitting member, the first fitting member and the second fitting member form an elastic embedding fit. The swing head mechanism facilitates an operator to set different swing angles of a stapler head portion, and can avoid uncontrollable swing of the stapler head portion.

20 Claims, 22 Drawing Sheets

(51) Int. Cl.
*A61B 17/068* (2006.01)
*A61B 17/29* (2006.01)

(52) U.S. Cl.
CPC ... *A61B 17/068* (2013.01); *A61B 2017/07214* (2013.01); *A61B 2017/2927* (2013.01)

(58) Field of Classification Search
CPC .......... A61B 2017/00022; A61B 2017/07214; A61B 2017/00477; A61B 2017/2927; A61B 2017/2929
USPC .............. 227/19, 175.1, 175.2, 176.1, 180.1; 606/1, 139, 219
See application file for complete search history.

(56) References Cited

U.S. PATENT DOCUMENTS

| | | | | |
|---|---|---|---|---|
| 6,981,628 | B2 * | 1/2006 | Wales | A61B 17/07207 227/180.1 |
| 7,624,902 | B2 * | 12/2009 | Marczyk | A61B 17/07207 227/176.1 |
| 7,963,431 | B2 * | 6/2011 | Scirica | A61B 17/07207 227/19 |
| 8,061,576 | B2 * | 11/2011 | Cappola | A61B 17/0682 227/176.1 |
| 8,336,754 | B2 * | 12/2012 | Cappola | A61B 17/07207 227/19 |
| 8,573,463 | B2 * | 11/2013 | Scirica | A61B 17/068 227/179.1 |
| 8,789,741 | B2 * | 7/2014 | Baxter, III | A61B 17/07207 227/176.1 |
| 9,445,810 | B2 * | 9/2016 | Cappola | A61B 17/07207 |
| 9,814,463 | B2 * | 11/2017 | Williams | A61B 17/07207 |
| 10,849,621 | B2 * | 12/2020 | Whitfield | A61B 90/03 |
| 2004/0193212 | A1 | 9/2004 | Taniguchi et al. | |

FOREIGN PATENT DOCUMENTS

| | | |
|---|---|---|
| CN | 105596049 A | 5/2016 |
| CN | 205514739 U | 8/2016 |
| CN | 106510784 A | 3/2017 |
| CN | 107970052 A | 5/2018 |
| CN | 109498089 A | 3/2019 |
| CN | 211270936 U | 8/2020 |
| JP | H1043190 A | 2/1998 |
| JP | 2002233967 A | 8/2002 |
| JP | 2006198152 A | 8/2006 |
| JP | 2011238447 A | 11/2011 |

OTHER PUBLICATIONS

International Search Report issued on Feb. 10, 2021 for International Patent Application No. PCT/CN2020/128287 (4 pages).
Japanese Office Action issued on Jun. 6, 2023 for Japanese Patent Application No. 2022-531517 (6 pages).

* cited by examiner

ROTATING MECHANISM AND SURGICAL STAPLER

CROSS-REFERENCE TO RELATED APPLICATIONS

This application is based upon PCT patent application No. PCT/CN2020/128287, filed on Nov. 12, 2020, which claims priority to Chinese Patent Applications No. 201911195242.X and 201922094449.X, filed on Nov. 28, 2019 and No. 202020538343.4, filed on Apr. 13, 2020, the entire contents of which are incorporated herein by reference.

TECHNICAL FIELD

The present disclosure relates to medical instruments' technology, more particularly, to a rotating mechanism and a surgical stapler.

BACKGROUND

A linear surgical stapler generally includes an instrument body and a head assembly mounted on the instrument body. The instrument body includes a firing handle, the head assembly includes a longitudinal shaft and a stapler head mounted at a distal side of the longitudinal shaft. The stapler head executes the actions of suturing and cutting. When driven by the firing handle, a firing assembly can drive the stapler head assembly to complete the suturing and cutting operation.

A rotating rod is arranged in the longitudinal shaft to rotate the stapler head assembly relative to the longitudinal shaft. A proximal end of the rotating rod is connected to a rotating driver, and a distal end of the rotating rod is rotatably fixed to a proximal side of the stapler head. When a rotating driver drives the rotating rod to move along an axial direction of the longitudinal shaft, the distal side of the rotating rod drives the stapler head to rotate clockwise or counterclockwise relative to the longitudinal shaft.

When the stapler head of an existing linear stapler rotates, the rotating angle is hard to control, and the stapler head may rotate uncontrollably when the stapler is used. Therefore, the rotating angle of the stapler head is uncontrollable, and the stapler head cannot be positioned precisely, affecting the operation effect.

In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site.

SUMMARY

To solve the problems in the prior art, the present disclosure provides a rotating mechanism and a surgical stapler, wherein, with the elastic inserted cooperation of the rotating component and the housing, different rotating angles can be conveniently achieved by the operator, and uncontrollable rotation of the stapler head can be prevented.

In the present disclosure, a rotating mechanism used for a surgical stapler is provided, the surgical stapler includes:

a rotating component, wherein an outer surface of the rotating component is provided with at least one first cooperating member;

a rotating rod cooperated with the rotating component, so that the rotating rod is moved along an axial direction of the stapler when the rotating component rotates;

a housing provided with an accommodating cavity for receiving the rotating component, wherein an inner side of the accommodating cavity is provided with at least one second cooperating member:

wherein the first cooperating member or the second cooperating member is elastic, when the rotating component rotates relative to the housing until the first cooperating member faces the second cooperating member, the first cooperating member and the second cooperating member form inserted cooperation.

In some embodiments, the first cooperating member includes an elastic convex portion, the second cooperating member includes a recess; or, the first cooperating member includes a recess, the second cooperating member includes an elastic convex portion.

In some embodiments, the first cooperating member includes an elastic convex portion, the second cooperating member includes a recess; the outer surface of the rotating component is provided with at least one of elastic sheet, the convex portion is formed between two ends of the elastic sheet, the convex portion protrudes toward a direction away from the central axis of the rotating component, compared to the two ends of the elastic sheet.

In some embodiments, at least one end of the elastic sheet is fixed to the rotating component.

In some embodiments, the outer surface of the rotating component is provided with two mounting grooves corresponding to the two ends of each elastic sheet, the two ends of the elastic sheet are mounted in the corresponding mounting grooves.

In some embodiments, each of the mounting grooves includes at least one extension section and at least one inclined section connected to a first end of the extension section, an angle forms between the inclined section and the extension section, and the extension section is connected to the outer surface of the rotating component; at least one end of the elastic sheet is located in the extension section, and the convex portion of the elastic sheet partially enters the inclined section.

In some embodiments, the mounting groove corresponding to at least one end of the elastic sheet further includes at least one fixed section connected to a second end of the extension section, an angle forms between the fixed section and the extension section, and the fixed section receives one end of the elastic sheet.

In some embodiments, the first cooperating member includes an elastic convex portion, the second cooperating member includes a recess: at least one metal ring is sleeved on the outer surface of the rotating component, and the at least one convex portion is formed on the metal ring.

In some embodiments, a part of the outer surface of the rotating component is concave inward to form a mounting groove, and the metal ring is inserted in the mounting groove.

In some embodiments, the mounting groove is annular, the metal ring is annular, and at least one of two ends of the metal ring is fixed to the rotating component.

In some embodiments, the first cooperating member includes a recess, the second cooperating member includes an elastic convex portion, the inner side of the accommodation cavity is provided with a fixed component and an annular elastic component surrounding the fixed component, the at least one convex portion is formed on the annular elastic component.

In some embodiments, the fixed component is annular to be adapted to the shape of the annular elastic component, and an opening is provided at a position corresponding to each convex portion on the fixed component.

In some embodiments, a gap is formed between the annular elastic component and the inner wall of the accommodating cavity.

In some embodiments, the first cooperating member includes a recess, the second cooperating member includes an elastic convex portion; the inner side of the accommodating cavity is provided with a fixed component and at least one elastic sheet fixed to the fixed component, the convex portion is formed between two ends of the elastic sheet.

In some embodiments, the first cooperating member is a convex portion, seen from the top view of the rotating component, a central line of each convex portion passes a center of the rotating component or doesn't pass a center of the rotating component;

or, the second cooperating member is a convex portion, seen from the top view of the accommodating cavity, a central line of each convex portion passes a center of the accommodating cavity or doesn't pass a center of the accommodating cavity.

In some embodiments, the convex portion includes an inclined first guiding surface and an inclined second guiding surface, so that a width of one end of the convex portion facing toward the recess is less than a width of another end of the convex portion away from the recess.

In some embodiments, there are a plurality of recesses including at least one initial position recess and at least one non-initial position recess, a depth of the initial position recess is larger than a depth of the non-initial position recess.

In some embodiments, the rotating component includes:

a rotating shaft cooperated with the rotating rod, so that the rotating rod is moved along an axial direction of the stapler when the rotating shaft rotates:

a rotating block cooperated with the rotating shaft, so that the rotating block is rotated when the rotating shaft rotates, wherein an outer surface of the rotating block is provided with the at least one first cooperating member.

In some embodiments, an outer surface of the rotating shaft is provided with at least one first cooperating portion, a first through hole is provided in the rotating block, and an inner side of the first through hole is provided with at least one second cooperating portion, the rotating shaft passes through the first through hole, and the first cooperating portion of the rotating shaft non-rotatably cooperates with the second cooperating portion of the rotating block.

In some embodiments, the rotating mechanism further includes an end cover provided above the rotating block, a second through hole is provided in the end cover, the rotating shaft passes through the second through hole; a bottom portion of the end cover is provided with at least one limit column, the housing is further provided with at least one fixed groove for the end cover, in which the limit column is inserted; the rotating mechanism further includes a rotating knob connected to an upper portion of the rotating shaft, a rotation of the rotating knob rotates the rotating shaft.

In some embodiments, the rotating block includes a shaft cooperating portion and a component mounting portion, the shaft cooperating portion is located above the component mounting portion, the first cooperating member is provided on an outer surface of the component mounting component, a diameter of the shaft cooperating portion is larger than or smaller than a diameter of the component mounting portion.

In some embodiments, the first cooperating member includes a recess, the second cooperating member includes an elastic convex portion, a cover plate is further provided between the shaft cooperating portion and the component mounting portion, an outer diameter of the cover plate is larger than an outer diameter of the component mounting portion, and the cover plate covers an upper surface of the convex portion.

In some embodiments, the first cooperating member includes an elastic convex portion, the second cooperating member includes a recess, an outer diameter of the component mounting portion at a position corresponding to the first cooperating member is smaller than an outer diameter of the component mounting portion at other positions.

In some embodiments, the rotating mechanism further includes a connecting component, a bottom portion of the rotating shaft is provided with a plate-shaped base, which is connected to the rotating rod through the connection component, and the plate-shaped base is eccentrically connected to the connecting component.

The present disclosure further provides a surgical stapler including the rotating mechanism.

The rotating mechanism and the surgical stapler of the present disclosure have the following advantages.

The present disclosure provides a rotating mechanism used for a surgical stapler, wherein, with the elastic inserted cooperation between the rotating component and the housing, the operator can set different rotating angles of the stapler head. The rotating angle of the stapler head can be precisely controlled by precisely controlling the axial moving distance of the rotating rod cooperating with the rotating component. Besides, when no external force is applied, the elastic inserted cooperation between the rotating component and the housing is relatively stable. Therefore, an uncontrollable rotation of the stapler head is prevented.

BRIEF DESCRIPTION OF THE DRAWINGS

Embodiments of the present disclosure will now be described, by way of example only, with reference to the accompanying schematic drawings. Apparently, the following figures are only exemplary. For the skilled in the art, other figures can also be gotten according to the following figures without creative work.

DETAILED DESCRIPTION

Figure 1:
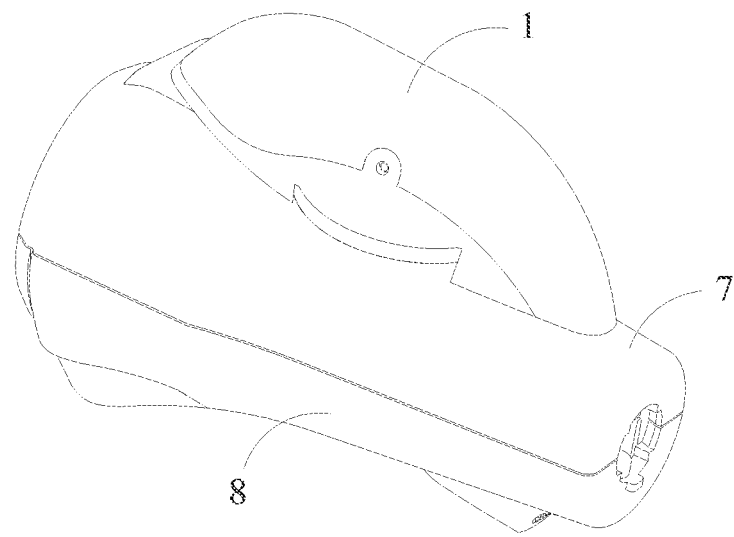
FIG. 1 is a structural schematic view of a rotating mechanism according to a first embodiment of the present disclosure.
Figure 2:
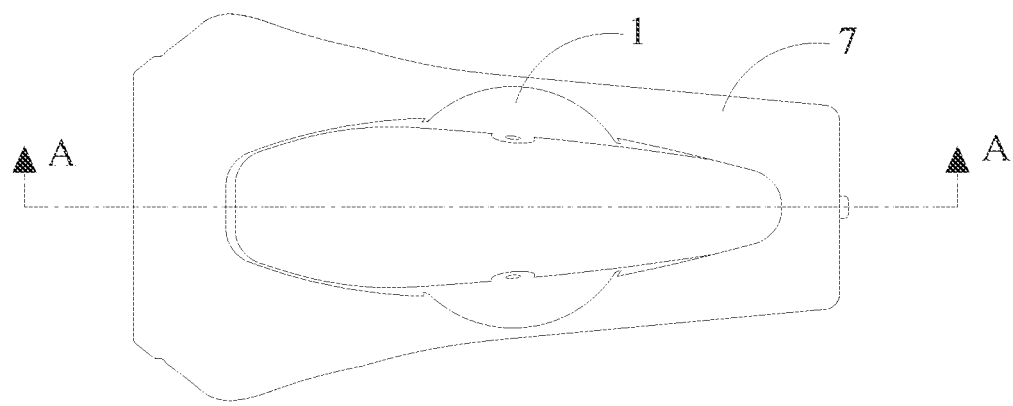
FIG. 2 is a top view of the rotating mechanism according to the first embodiment of the present disclosure.
Figure 3:
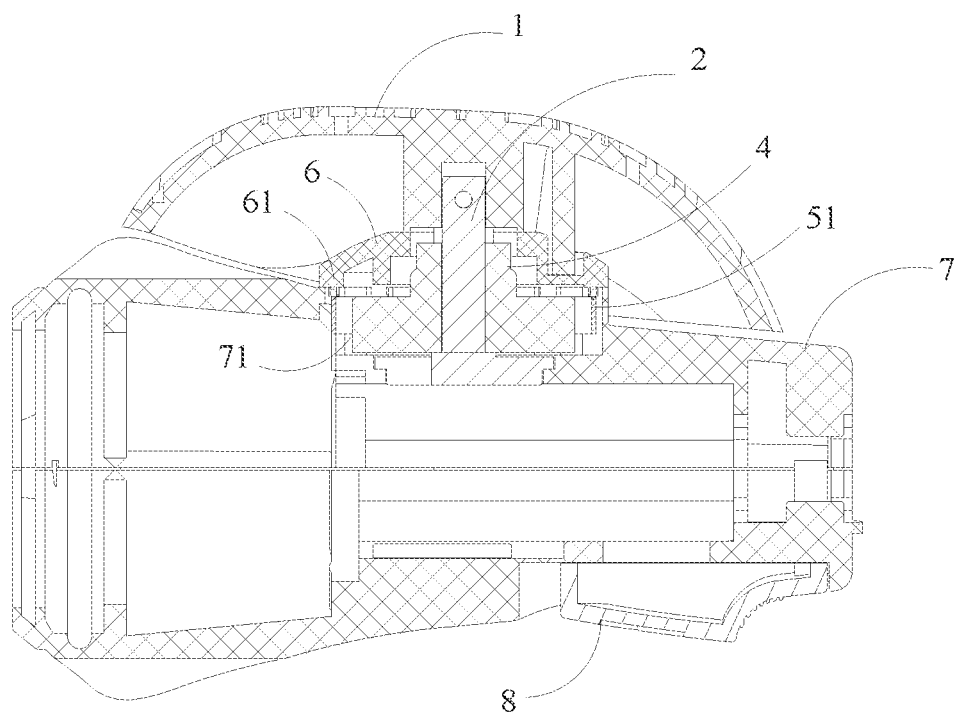
FIG. 3 is a section view of FIG. 2 along A-A direction.

Embodiments of the present disclosure will now be described, by way of example only, with reference to the accompanying schematic drawings according to embodiments of the present disclosure, to make the objective, technical proposal and advantages clearer. It should understand that the embodiment described are only a part of embodiments of the present disclosure, and are not intended to be a limitation to the protection scope of the present disclosure.

To solve the technical problem of the existing technology, the present disclosure provides a rotating mechanism used for a surgical stapler and a surgical stapler including the rotating mechanism. The stapler includes an instrument body and a head assembly. The head assembly includes a longitudinal shaft and a stapler head. The instrument body includes a rotating mechanism to rotate the stapler head relative to the longitudinal shaft. The rotating mechanism includes a housing, a rotating component, and a rotating rod. The housing is provided with an accommodating cavity for receiving the rotating component, the rotating component cooperates with the rotating rod, so that when the stapler head is needed to rotate, the operator can rotate the rotating component to move the rotating rod along an axial direction of the stapler, to rotate the stapler head.

To facilitate the operator to rotate the stapler head at different rotating angles and prevent uncontrolled rotation, an outer surface of the rotating component is provided with at least one first cooperating member. An inner side of the accommodating cavity is provided with at least one second cooperating member cooperated with the first cooperating member. The first cooperating member or the second cooperating member is elastic. When the rotating component rotates relative to the housing until the first cooperating member faces the second cooperating member, the first cooperating member and the second cooperating member form inserted cooperation.

Therefore, when the operator rotates the rotating portion to rotate the stapler head, after the first cooperating member and the second cooperating member form inserted cooperation, a resistance and a lagging happen under the effect of the inserted cooperation. Therefore, the rotating component stops at a position when the first cooperating member faces the second cooperating member, so that the rotating component is kept still. When the operator further rotates the rotating component, the rotating force will overcome the elastic deformation force of the first cooperating member or the second cooperating member to separate the first cooperating member from the second cooperating member. Therefore, the rotating component can go on rotating until the next first cooperating member faces the second cooperating member. As the position of the second cooperation component corresponds to the rotating angle of the stapler head, the rotating angle of the rotating component can be set by setting the position of the second cooperating member. Then different rotating angles of the stapler head can be achieved. During operation, the elastic inserted cooperation is relatively stable, so that the stapler head can be kept in a relatively stable state without manually external force, to prevent an uncontrollable rotation of the stapler head.

In the following, the structure of the rotating mechanism according to a plurality of specific embodiments is described. It should be noted that the specific embodiments are not used for a limitation to the protection scope of the present disclosure.

In the first embodiment, the second embodiment and the third embodiment shown in FIGS. 1-24, the first cooperating member includes an elastic convex portion, the second cooperating member includes a recess. When the rotating component rotates relative to the housing until the convex portion faces the recess, the convex portion at least partially enters the recess, to form elastic inserted cooperation between the convex portion and the recess. The elastic inserted cooperation in the embodiment means that when the convex portion at least partially enters the recess, and no external force is applied, the convex portion and the recess form relatively stable cooperation, to keep the rotating component at its current position. When an external force is applied to rotate the rotating component, the elastic deformation force of the convex portion is overcome, so as to separate the convex portion from the recess, then the rotating component can rotate relative to the housing.

FIGS. 1-16 show the structure of the rotating mechanism according to the first embodiment of the present disclosure. As shown in FIGS. 1-6, in the embodiment, the rotating mechanism includes a rotating component, a rotating rod 93 and a housing. The rotating component cooperates with the rotating rod 93, so that when the rotating component rotates, the rotating rod 93 is moved along an axial direction of the stapler. For example, when the rotating component rotates along a first direction, the rotating rod 93 is moved toward a distal side of the stapler, when the rotating component rotates along a second direction, the rotating rod 93 is moved toward a proximal side of the stapler.

Figure 7:
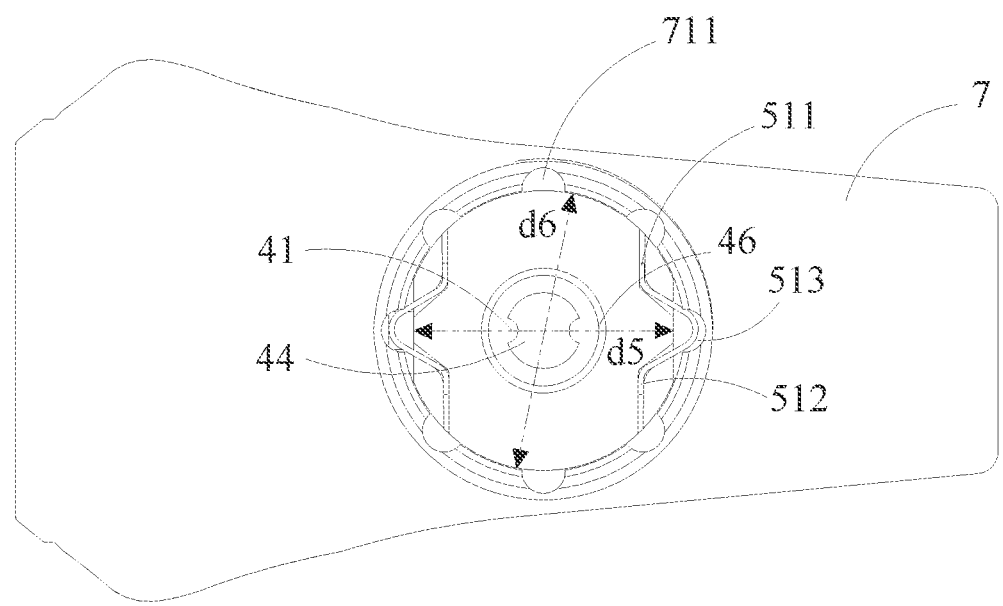
FIG. 7 is a structural schematic view of the rotating mechanism after the knob is removed according to the first embodiment of the present disclosure.

In the embodiment, the first cooperating member includes an elastic convex portion 513, the second cooperating member includes a recess 711. The rotating mechanism further includes at least one elastic sheet 51. At least a part of the elastic sheet 51 protrudes from the outer surface of the rotating component. The elastic sheet 51 includes at least one convex portion 513. The convex portion 513 protrudes toward a direction away from a rotating shaft of the rotating component. The housing includes an upper housing 7 and a bottom housing. An inner peripheral portion of the upper housing 7 is provided with an accommodating cavity 71 for receiving the rotating component, and an inner wall of the accommodating cavity 71 is provided with the at least one recess 711. As shown in FIG. 7, when the rotating component rotates relative to the housing, until the convex portion 513 faces the recess 711, the convex portion 513 at least partially enters the recess 711, so that the convex portion 513 and the recess 711 form elastic inserted cooperation. The elastic inserted cooperation here means that when the convex portion 513 at least partially enters the recess 711, and no external force is applied, the convex portion 513 and the recess 711 form relatively stable cooperation, to keep the rotating component at its current position. When an external force is applied to rotate the rotating component, the elastic deformation force of the convex portion 513 is overcome, to separate the convex portion 513 from the recess 711, then the rotating component can rotate relative to the upper housing 7.

Therefore, when the operator rotates the rotating component, a resistance and a lagging will happen after the convex portion 513 at least partially enters the recess 711, so the convex portion 513 is kept in the recess 711. When the operator further rotates the rotating component, the rotating force will overcome the elastic deformation force of the convex portion 513 to separate the convex portion 513 from the recess 711. Then the rotating component can further rotates until the convex portion 513 enters the next recess 711, and is kept in the next recess 711. As the position of the recess 711 corresponds to the rotating angle of the stapler, the rotating angle of the rotating component can be set by setting the position of the recess 711, and different rotating angles of the stapler head can be achieved. Therefore, a plurality of recesses 711 can be provided in turn on the inner peripheral portion of the upper housing 7, to achieve different rotating angles of the stapler head. During operation, the elastic convex portion 513 and the recess 711 can form relatively stable cooperation, so that the stapler head can be kept in a relatively stable state without manually external force, to prevent uncontrollable rotation of the stapler head.

Figure 6:
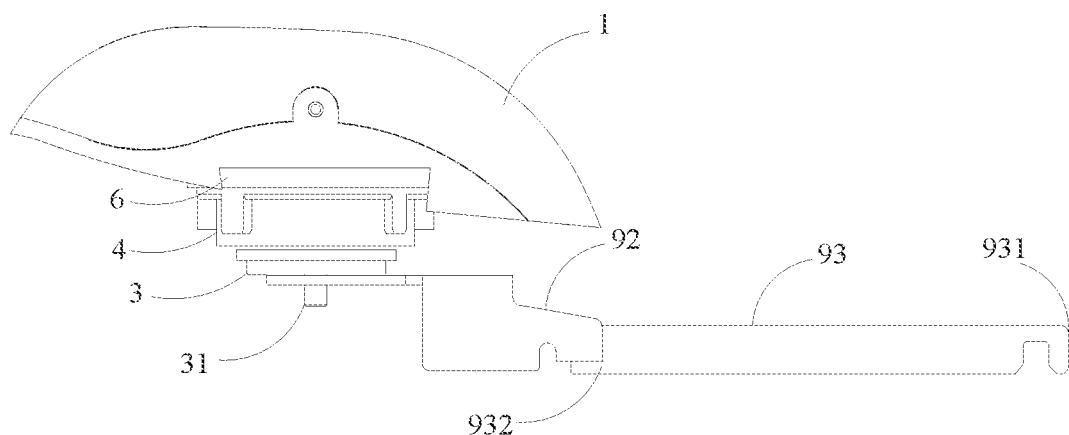
FIG. 6 is a structural schematic view of the rotating mechanism after the housing is removed according to the first embodiment of the present disclosure.

In the present disclosure, the terms "distal side" and "proximal side" are used herein with reference to an operator manipulating the stapler. The term "proximal side" refers to a side closer to the operator, and the term "distal side" refers to a side away from the operator, that is, a side closer to the surgical site. For example, in the view angle of FIG. 6, a right side of the rotating rod 93 is a distal side 931 connected to the stapler head, a left side of the rotating rod 93 is a proximal side 932 connected to a distal side 92 of the connecting component 9. Up and down are described in the view angle of FIG. 6. FIG. 7 shows the upper surface of the upper housing 7. As shown in FIG. 6, the rotating knob 1 is located above the end cover 6, the end cover 6 is located above the rotating block 4, the plate-shaped base 3 is located below the rotating block 4. In the present disclosure, for a component, inner side and outer side are defined relative to a central axis of the component. Wherein, inner side is a side closer to the central axis, outer side is a side away from the central axis.

Figure 4:
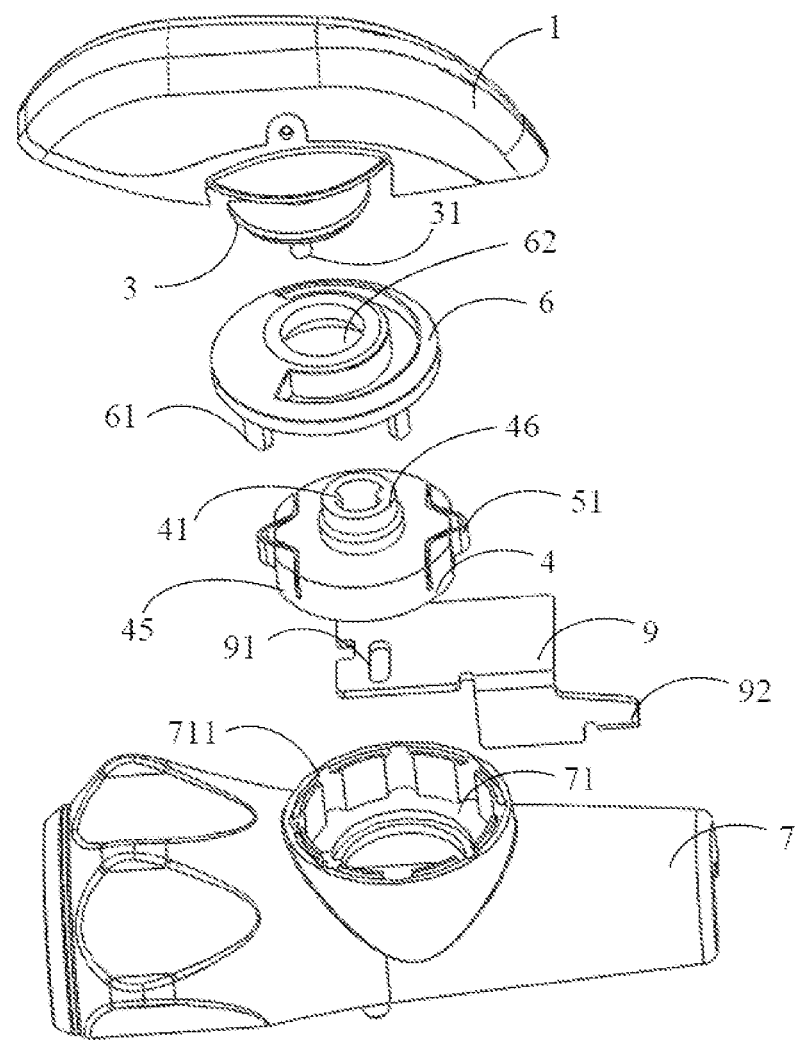
FIG. 4 and FIG. 5 are exploded views of the rotating mechanism according to the first embodiment of the present disclosure.
Figure 5:
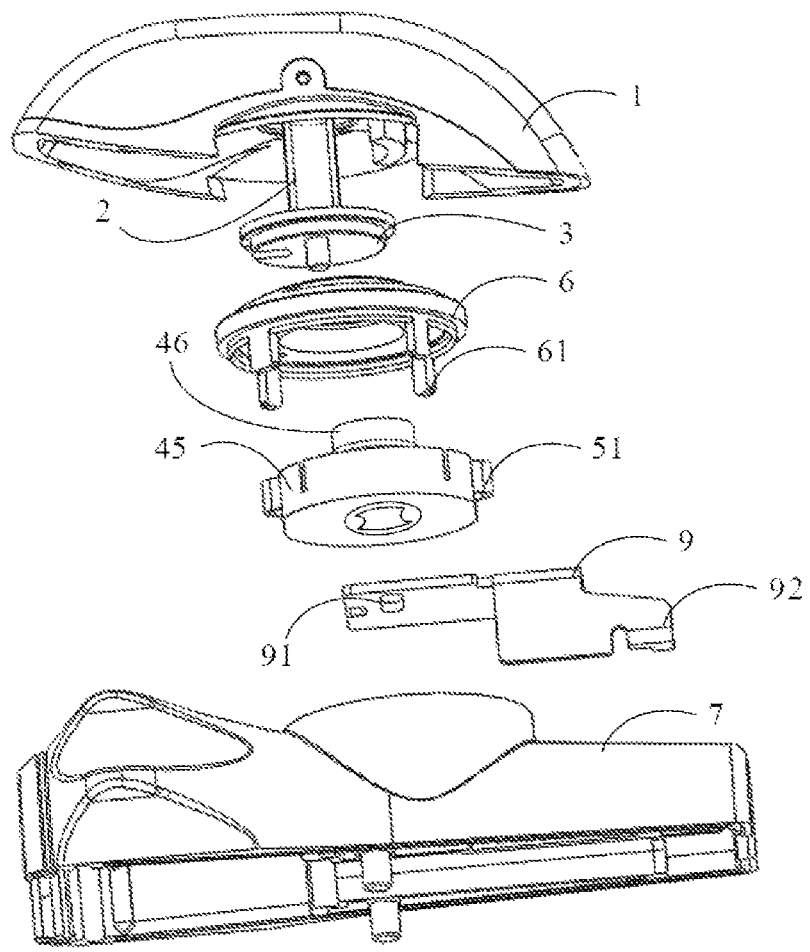

As shown in FIGS. 4-6, the rotating component includes a rotating shaft 2 and a rotating block 4, the rotating block 4 is provided with a first through hole 44. The rotating shaft 2 passes through the first through hole 44. A bottom portion of the rotating shaft 2 is provided with a plate-shaped base 3 connected to the rotating rod 93 through a connecting component 9, and a distal side 92 of the connecting component 9 is connected to the rotating rod 93. The plate-shaped base 3 is eccentrically connected to the connecting component 9. Specifically, a bottom portion of the plate-shaped base 3 is provided with a convex shaft 31, the connecting component 9 is provided with a waist-shaped cooperating hole 91. The convex shaft 31 passes through the cooperating hole 91. The direction from a proximal side toward a distal side of the stapler head is defined as an axial direction of the stapler. Preferably, the cooperating hole 91 is perpendicular to the axial direction of the stapler. In other embodiments, a cooperating hole can be provided on a bottom portion of the plate-shaped base 3, and a convex shaft passing though the cooperating hole is provided on the connecting component 9. The plate-shaped base 3 and the rotating shaft 2 can be integrally formed, or the plate-shaped base 3 and the rotating shaft 2 can be two independent components fixedly connected with each other. When the rotating shaft 2 rotates, the plate-shaped base 3 is rotated, the connecting component 9 can be moved along the axial direction of the stapler for the eccentric cooperation between the plate-shaped base 3 and the connecting component 9, then the rotating rod 93 can be moved along the axial direction of the stapler.

As shown in FIGS. 4-6, in the embodiment, the rotating mechanism further includes an end cover 6 provided above the rotating block 4. The end cover 6 is provided with a second through hole 62, and the rotating shaft 2 passes through the second through hole 62. A bottom portion of the end cover 6 is provided with a plurality of limit columns 61. The housing is further provided with a plurality of fixed grooves for the end cover 6, and the limit columns 61 are inserted in the fixed grooves for the end cover 6. The end cover 6 can limit the axial position of the rotating block 4, to prevent the rotating block 4 from separating from the upper portion of the accommodating cavity 71 or moving up and down. The rotating block 4 is located in a space defined by the end cover 6 and the accommodating cavity 71. The rotating block 4 can only rotate relative to the upper housing 7, and cannot move along an axial direction of the rotating block 4.

As shown in FIGS. 7-13, an outer surface of the rotating block 4 is provided with the elastic sheet 51. In the embodiment, the rotating block 4 includes a first step portion 46 and a component mounting portion 45. The first step portion 46 is located above the component mounting portion 45, the first cooperating member is mounted on an outer surface of the component mounting portion 45. A diameter of the first step portion 46 is smaller than a diameter of the component mounting portion 45. The first step portion 46 is used as a shaft cooperating portion cooperated with the rotating shaft 2. The shape of the inner portion of the end cover 6 and the shape of the accommodating cavity 71 of the upper housing 7 are both formed to adapt to the structure of the rotating block 4.

As shown in FIG. 7, in an embodiment, there are a plurality of recesses 711 in the accommodating grove 71 of the upper housing 7. Each recess 711 has the same shape and size, and each recess 711 has the same depth. That is, in the top view of the upper housing 7, a distance between a point of each recess 711 farthest to the center of the accommodating cavity 71 and the center of the accommodating cavity 71 is the same.

Figure 8:
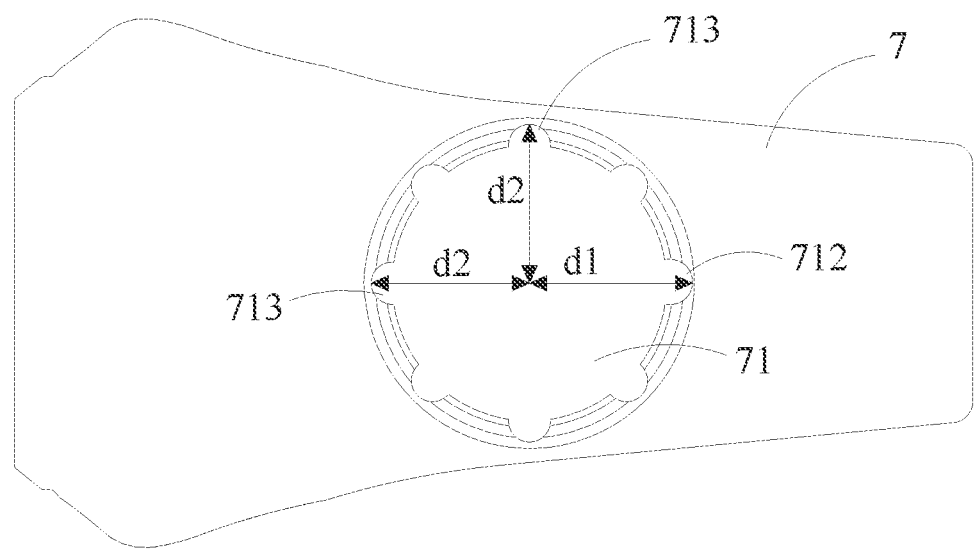
FIG. 8 is a top view of an upper housing having recesses with different depths according to the first embodiment of the present disclosure.
Figure 9:
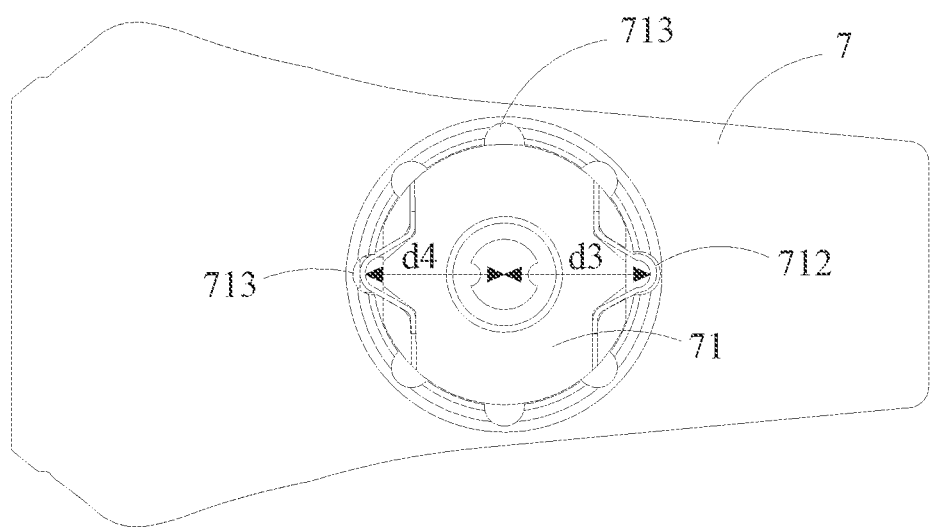
FIG. 9 is a top view showing the upper housing with different depths cooperating with elastic sheets according to the first embodiment of the present disclosure.

As shown in FIG. 8 and FIG. 9, in another embodiment of the present disclosure, the recesses 711 can have different depths. For example, the recesses 711 can be divided into two kinds: at least one initial position recess 712 and at least one non-initial position recess 713. A depth of the initial position recess 712 is larger than a depth of the non-initial position recess 713. The initial position recess 712 is located on the axial direction of the stapler. As shown in FIG. 8, in the top view of the accommodating cavity 71, a distance between a point of the initial position recess 712 farthest to the center of the accommodating cavity 71 and the center of the accommodating cavity 71 is d1. A distance between a point of the non-initial position recess 713 farthest to the center of the accommodating cavity 71 and the center of the accommodating cavity 71 is d2. Wherein d1 is larger than d2. When the convex portion 513 of the elastic sheet 51 is in the initial position recess 712, a distance between a point of the convex portion 513 farthest to the center of the accommodating cavity 71 and the center of the accommodating cavity 71 is d3. When the elastic sheet 51 is in the non-initial position recess 713, a distance between a point of the convex portion 513 farthest to the center of the accommodating cavity 71 and the center of the accommodating cavity 71 is d4. Wherein d3 is larger than d4.

There can be one or more initial position recess 712, and one or more non-initial position recess 713. When the stapler head is in its initial position, the convex portion 513 of the elastic sheet 51 is in the initial position recess 712. As the rotating block 4 rotates, the convex portion 513 of the elastic sheet 51 rotates and enters the non-initial position recess 713. The operator can sense the difference of the resistance to confirm the position of the initial position recess 712, and further precisely confirm the initial position of the stapler head, to realize a precise positioning of the initial position of the stapler head.

Figure 10:
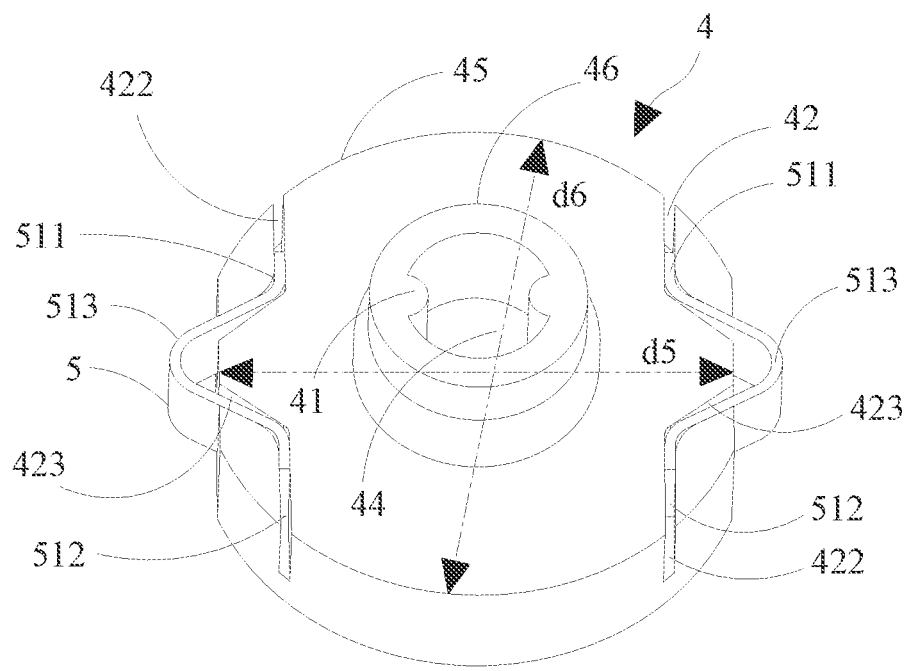
FIG. 10 is a structural schematic view showing a rotating block cooperating with the elastic sheet according to the first embodiment of the present disclosure.
Figure 11:
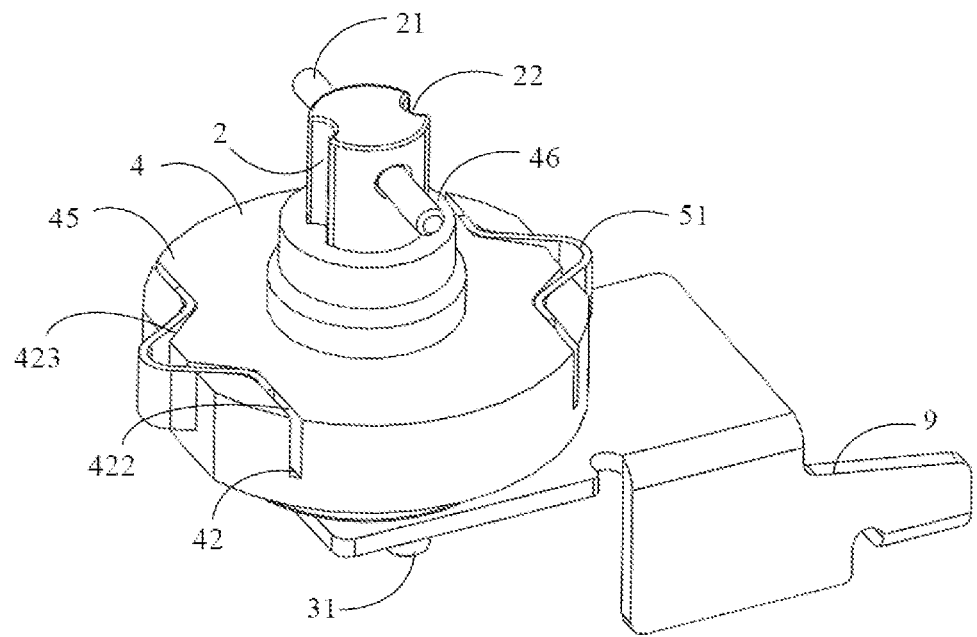
FIG. 11 is a stereogram of the rotating mechanism after the rotating knob and the housing are removed according to the first embodiment of the present disclosure.

As shown in FIGS. 10-13, the rotating mechanism includes a rotating knob 1 connected to an upper portion of the rotating shaft 2. The rotation of the rotating knob 1 can rotate the rotating shaft 2. In the embodiment, as shown in FIG. 11, the upper portion of the rotating shaft 2 is provided with a fixed pin 21, two ends of the fixed pin 21 are fixed on an inner surface of the rotating knob 1, to form a rotating coupling connection between the rotating knob 1 and the rotating shaft 2. As shown in FIG. 10 and FIG. 1, an outer surface of the rotating shaft 2 is provided with at least one first cooperating portion 22, a first through hole 44 is opened in the rotating block 4, and at least one second cooperating portion 41 is provided on the inner surface of the first through hole 44. The rotating shaft 2 passes through the first through hole 44, and the first cooperating portion 22 of the rotating shaft 2 is non-rotatably connected with the second cooperating portion 41 of the rotating block 4. In the embodiment, the first cooperating portion 22 is a groove located on the outer surface of the first rotating shaft 2, the second cooperating portion 41 is a convex strip located on the inner surface of the first through hole 44, and the convex strip is inserted in the groove of the rotating shaft 2. In other embodiments, the first cooperating portion can be a convex strip or a convex block located on the outer surface of the rotating shaft 2, and the second cooperating portion is a groove on the inner surface of the first through hole 44. In other embodiments, the first cooperating portion can be another fixed pin passing through the rotating shaft 2. The second cooperating portion includes blind holes located on the inner surface of the first through hole 44. Two ends of the fixed pin are inserted in the blind holes. The illustrated embodiments are all included in the protection scope of the present disclosure.

As shown in FIG. 10, one or more elastic sheet 51 can be provided on the outer surface of the rotating block 4. Correspondingly, as shown in FIG. 7, there are a plurality of the recesses 711. In the embodiment, the outer surface of the rotating block 5 is provided with two elastic sheets 51 relatively arranged, to realize more stable cooperation between the elastic sheets 51 and the recess 711. The present disclosure is not limited to this structure. The convex portion 513 is formed between a first end 511 and a second end 512 of the elastic sheet 51. The first end 511 and the second end 512 of the elastic sheet 51 are fixed to the outer surface of the rotating block 4, and the convex portion 513 protrudes from an outer periphery portion of the component mounting portion 45. The convex portion 513 protrudes toward a direction away from the rotating shaft of the component mounting portion 45, compared to the two ends 511, 512 of the elastic sheet 51. Preferably, as shown in FIG. 10 and FIG. 7, an outer diameter of the component mounting portion 45 at a position corresponding to the convex portion 513 is d5. An outer diameter of the component mounting portion 45 at other positions is d6, and d5 is smaller than d6.

Therefore, the accommodating space for the deformation of the convex portion 513 is big enough, so that the convex portion 513 won't be stuck with the accommodating cavity 71 and the rotating block 5 when the convex portion 513 is moved by the rotating knob 1, especially after the convex portion 513 is separated from the recess 711.

As shown in FIG. 10, corresponding to each of the elastic sheets 51, the outer surface of the rotating block 4 is provided with two mounting grooves 42 corresponding to the two ends of the elastic sheet 51. The two ends of the elastic sheets 51 are inserted in the two mounting grooves 42. Each of the mounting grooves 42 includes two extension sections 422 and two inclined sections 423 connected to first ends of the extension sections 422. An angle forms between one extension section 422 and one inclined section 423, and the inclined section 423 extend to the outer surface of the rotating block 4. The angle between the extension section 422 and the inclined section 423 is an obtuse angle ranging from 90 degrees to 180 degrees. Therefore, when the elastic sheet 51 is pressed by the inner wall of the accommodating cavity 71, the first end 511 and the second end 512 of the elastic sheet 51 extend toward two sides and the elastic sheet 51 is deformed. The end portions of the elastic sheet 51 are located in the extension sections 422, and the convex portion 513 of the elastic sheet 51 at least partially enters the inclined sections 423. Another end of each extension portion 422 can extend to the outer surface of the rotating block 4. When the elastic sheet 51 enters the recess 711 of the accommodating cavity 71, a redundant space exists between the first end 511 of the elastic sheet 51 and the second end 422 of one extension section 422, and a redundant space exists between the second end 512 of the elastic sheet 51 and the second end 422 of another extension section 422. Therefore, when the elastic sheet 51 is deformed, the first end 511 and the second end 512 of the elastic sheet 51 extend toward two sides, respectively.

Figure 12:
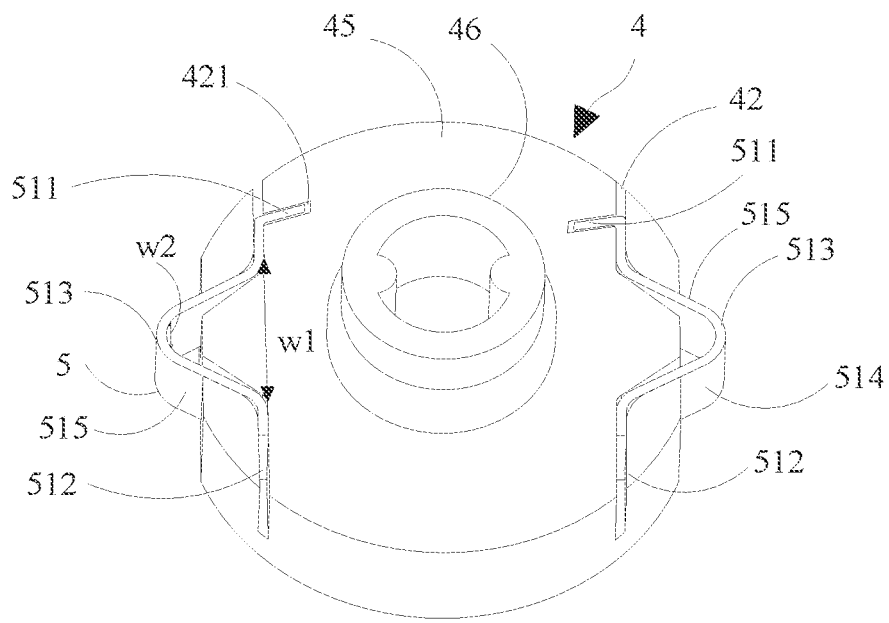
FIG. 12 is a structural schematic view showing a fixing way of the elastic sheets in the rotating block according to the first embodiment of the present disclosure.
Figure 13:
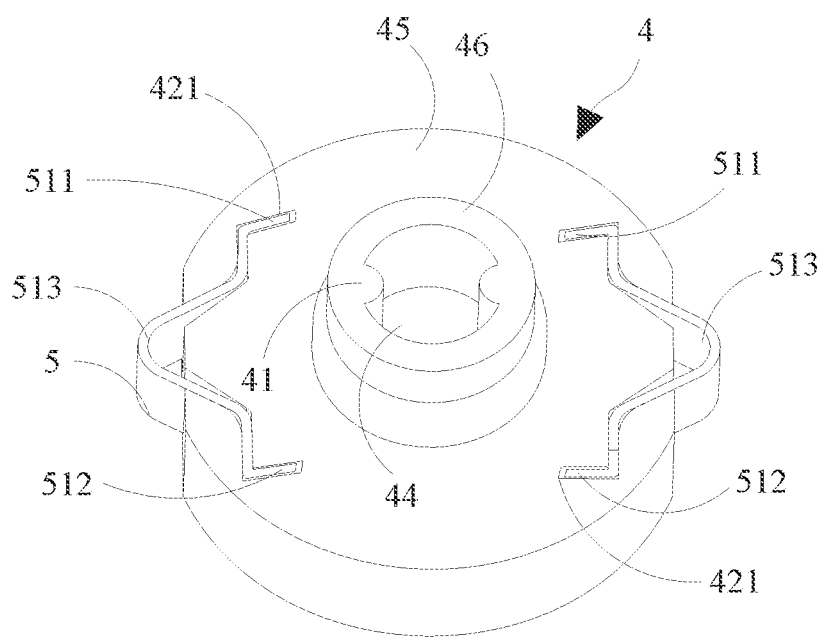
FIG. 13 is a structural schematic view showing another fixing way of the elastic sheets in the rotating block according to the first embodiment of the present disclosure.

FIG. 12 and FIG. 13 show that at least one end of the elastic sheet 51 is fixed to the rotating block 4. As shown in FIG. 12, the first end 511 of the elastic sheet 51 is fixed to the rotating block 4. As shown in FIG. 13, the first end 511 and the second end 512 are both fixed to the rotating block 4. The mounting groove 42 corresponding to the ends of the elastic sheet 51 fixed to the rotating block 4 further includes at least one fixed section 421 connected to the second end of the extension section 421. An angle forms between the fixed section 421 and the extension section 422, and the angle ranges from 0 degree to 180 degrees. The fixed section 421 receives the corresponding end portion of the elastic sheet 51. The end portion of the elastic sheet 51 can also be fixed to the rotating block 4 through other ways, for example, welding, riveting, etc.

As shown in FIG. 12, the convex portion 513 includes an inclined first guiding surface 514 and an inclined second guiding surface 515. Therefore, a width w2 of one end of the convex portion 513 away from the rotating block 4 is smaller than a width w1 of another end of the convex portion 513 close to the rotating block 4. In the embodiment, the end of the convex portion 513 away from the rotating block 4 is the end of the convex portion 513 facing toward the recess 711. The end of the convex portion 513 close to the rotating block 4 is the end of the convex portion 513 away from the recess 711. When the convex portion 513 rotates along with the rotating block 4, the first guiding surface 514 and the second guiding surface 515 can better guide the convex portion 513 to enter or separate from the recess 711 of the accommodating cavity 71. Preferably the first guiding surface 514 and the second guiding surface 515 are smooth surfaces, to make the rotating action smoother, and prevent an inconvenient operation caused by too big resistance.

Figure 14:
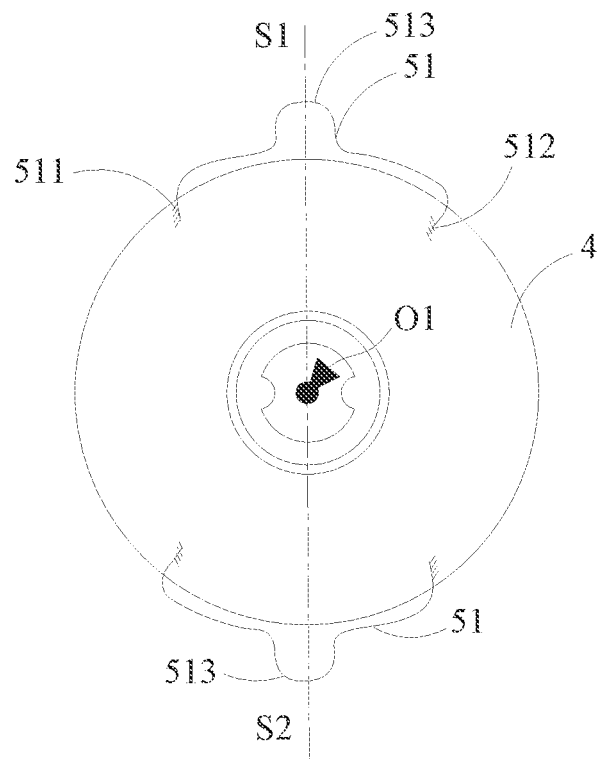
FIG. 14 is a top view of the rotating block cooperating with the elastic sheet according to the first embodiment of the present disclosure.
Figure 15:
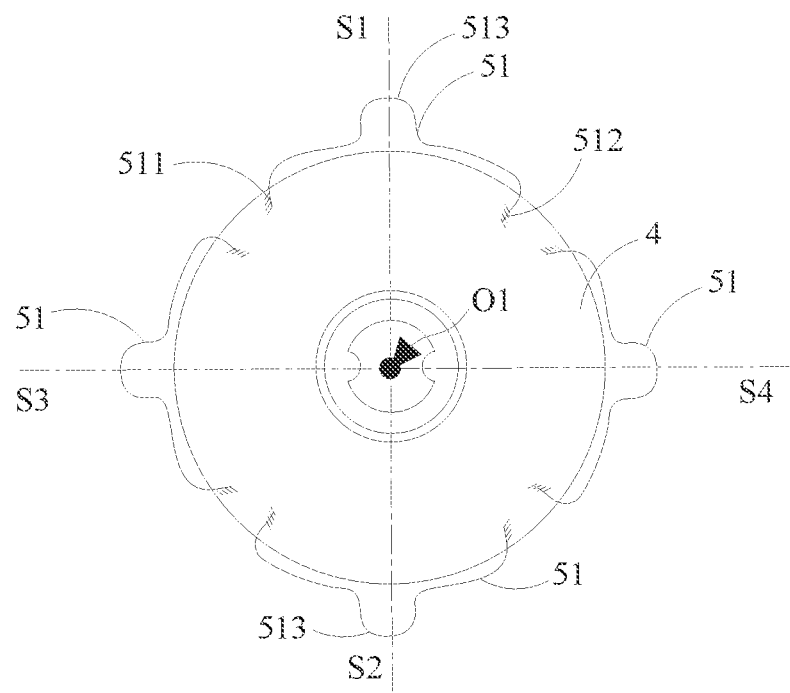
FIG. 15 is a top view showing arranging four elastic sheets in the rotating block according to the first embodiment of the present disclosure.

As shown in FIG. 14, in the embodiment, in the top view of the rotating block 4, the central line of each convex portion 513 passes through the center O1 of the rotating block 4. Here the central line of the convex portion 513 is a central line dividing equally the convex portion 513, seen in the top view of the rotating block 4. As shown in FIG. 14, the central lines S1 and S2 of the convex portions 513 of the two elastic sheets 51 both pass through the center O1 of the rotating block 4. FIG. 15 is the top view of a rotating block 4 provided with four elastic sheets, wherein the central lines S1, S2, S3 and S4 of the convex portions 513 of the four elastic sheets 51 all pass through the center O1 of the rotating block 4.

Figure 16:
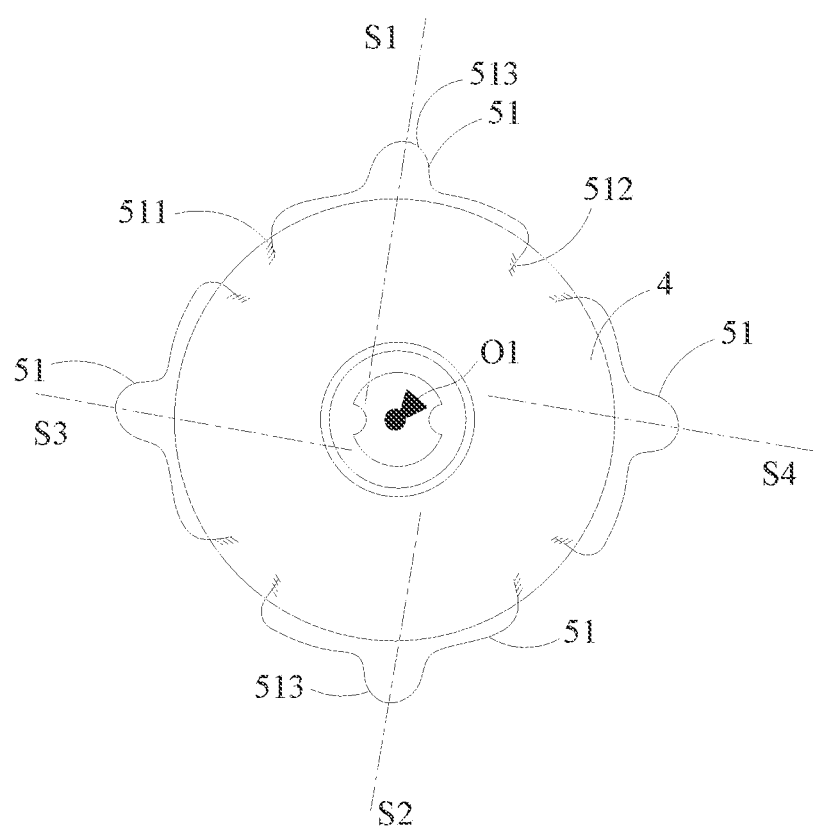
FIG. 16 is a top view showing arranging eccentric elastic sheets in the rotating block according to the first embodiment of the present disclosure.

FIG. 16 is the top view of the rotating block 4 in another embodiment. Wherein the central line of each convex portion doesn't pass through the center O1 of the rotating block 4. FIG. 15 is a top view of a rotating block 4 provided with four elastic sheets. Wherein none of the central lines S1, S2, S3 and S4 of the convex portions 513 of the four elastic sheets 4 passes through the center O1 of the rotating block 4. Therefore, when the rotating block 4 rotates clockwise or counterclockwise, the convex portion 513 can stably cooperate with the recess 71.

Figure 17:
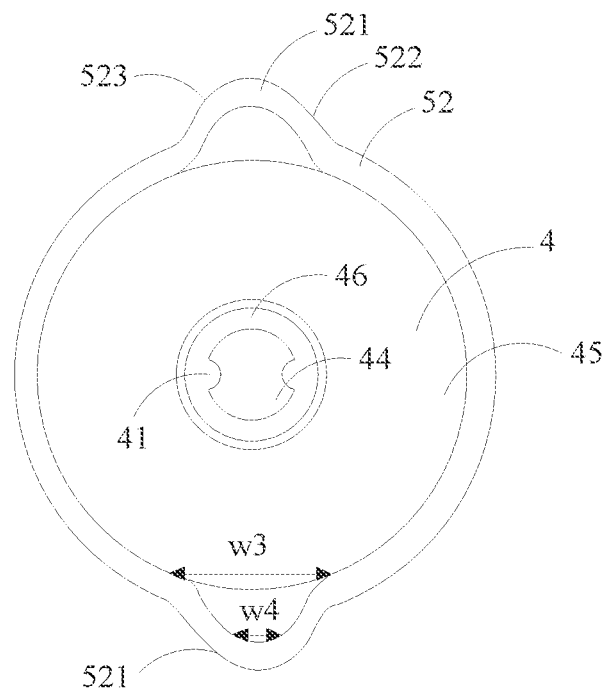
FIG. 17 is a structural schematic view showing a rotating block cooperating with a metal ring according to a second embodiment of the present disclosure.

FIGS. 17-20 show the structure of the rotating block cooperating with the first cooperating member of the rotating mechanism according to the second embodiment of the present disclosure. The difference between the second embodiment and the first embodiment is that, in the second embodiment, a metal ring 52 is provided on the outer surface of the rotating component. Specifically, the metal ring 52 is sleeved on the outer surface of the rotating block 4, and the at least one convex portion 521 is formed on the metal ring 52. As shown in FIG. 17, the convex portion 521 includes an inclined third guiding surface 522 and an inclined guiding surface 523. Therefore, a width w4 of one end of the convex portion 513 away from the rotating block 4 is smaller than a width w3 of another end of the convex portion 513 close to the rotating block 4, to better guide the convex portion 521 to enter or separate from the recess 711 of the accommodating cavity 71. The metal ring 52 can be formed by connecting one end to another end of a wire rope, but the present disclosure is not limited to this. In other embodiments, the metal ring 52 can also be formed by a circled copper wire or iron wire, etc.

Figure 18:
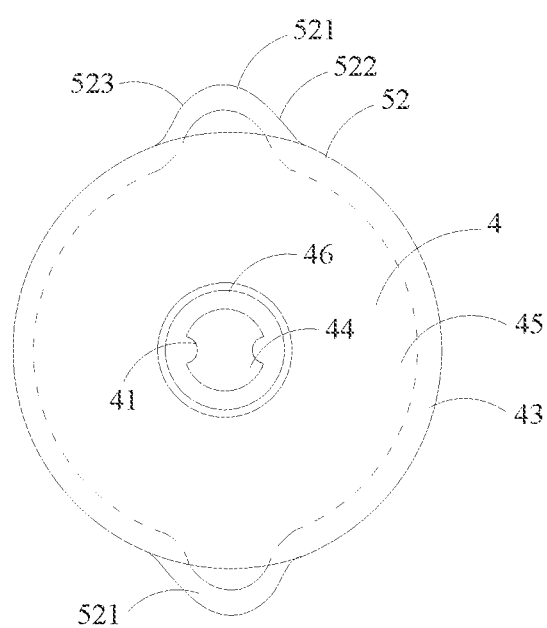
FIG. 18 is a structural schematic view showing the metal ring being inserted in the rotating block according to the second embodiment of the present disclosure.
Figure 19:
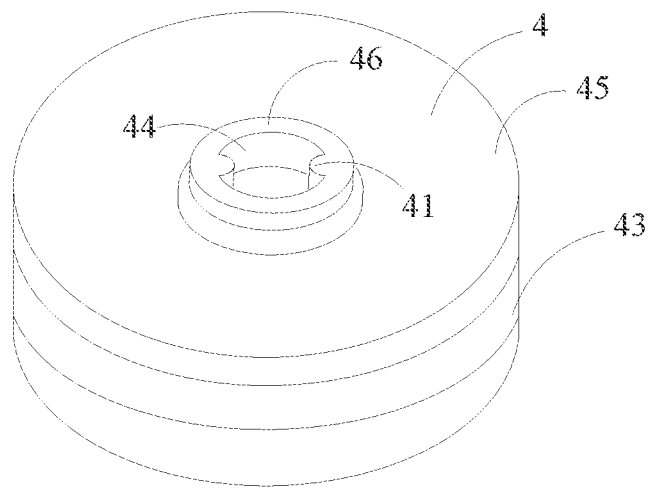
FIG. 19 is a structural schematic view of the rotating block according to the second embodiment of the present disclosure.
Figure 20:
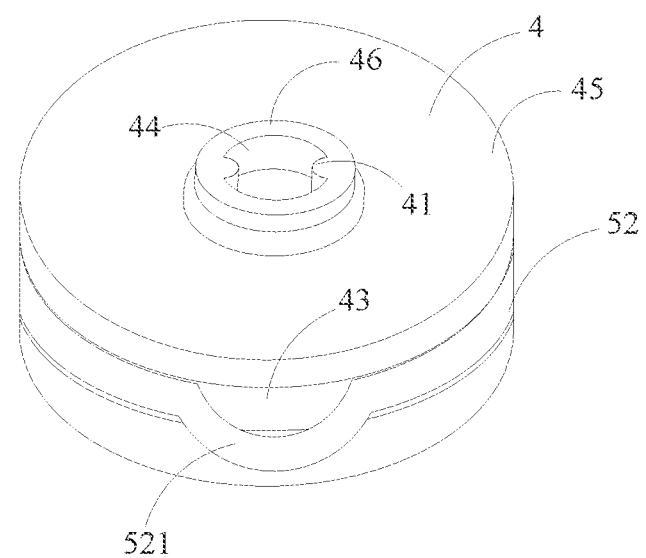
FIG. 20 is a stereogram showing the metal ring being inserted in the rotating block according to the second embodiment of the present disclosure.
Figure 21:
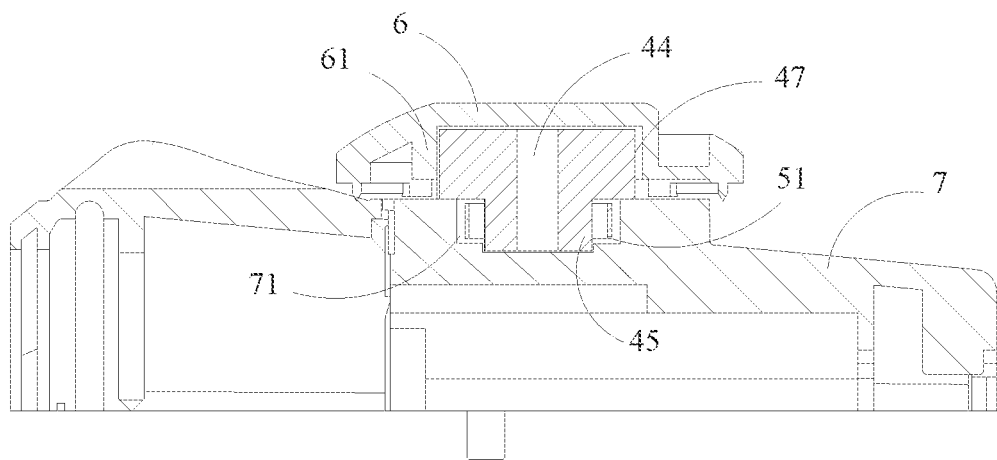
FIG. 21 is a structural schematic view showing the rotating block cooperating with an end cover and an upper housing according to a third embodiment of the present disclosure.
Figure 22:
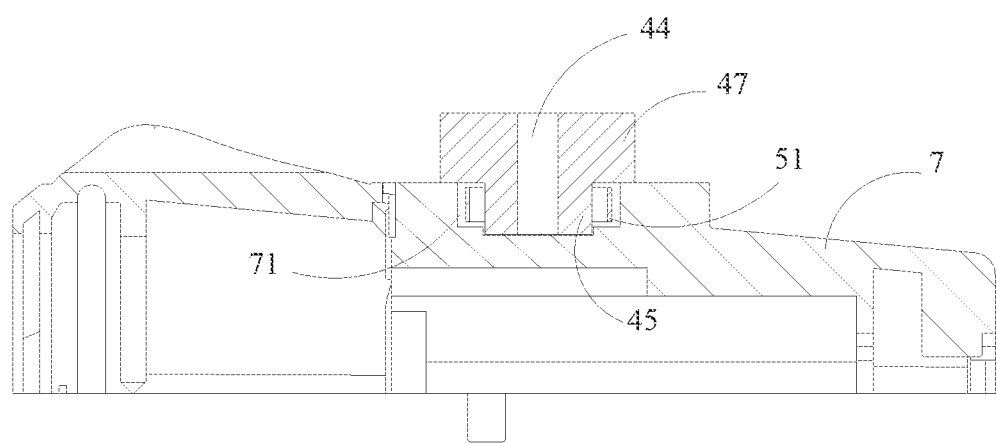
FIG. 22 is a structural schematic view showing the rotating block cooperating with the upper housing according to the third embodiment of the present disclosure.
Figure 23:
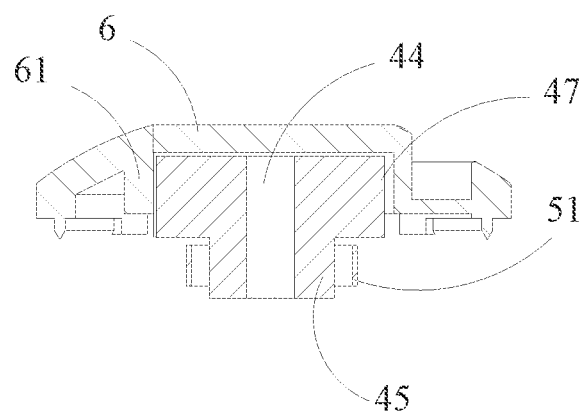
FIG. 23 is a structural schematic view showing the rotating block cooperating with the end cover according to the third embodiment of the present disclosure.
Figure 24:
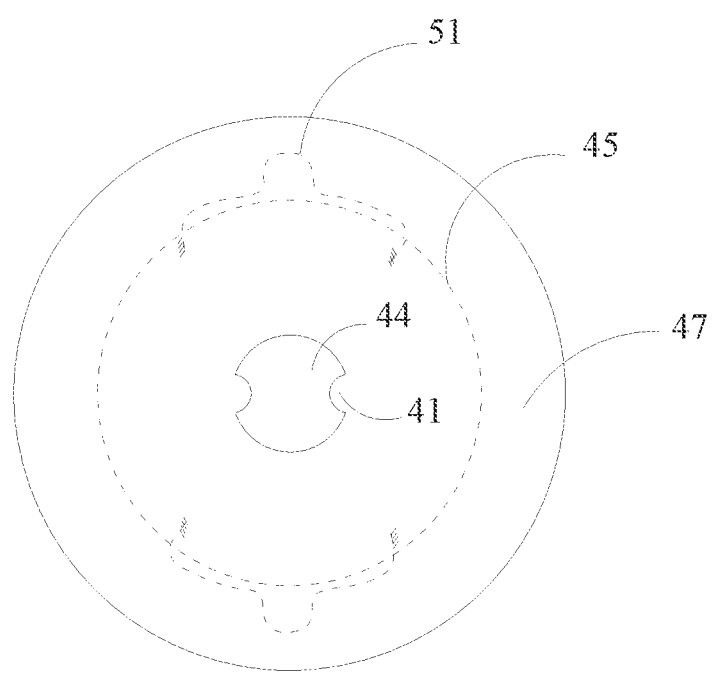
FIG. 24 is a top view of the rotating block according to the third embodiment of the present disclosure.

FIG. 17 and FIGS. 18-20 show two different ways of fixing the metal ring 52 on the rotating block 4. FIG. 17 shows that the metal ring 52 is clamped on the outer surface of the rotating block 4. FIGS. 18-20 show that the metal ring 52 is inserted in a mounting groove 43 for the metal ring 52 on the outer surface of the rotating block 4, the mounting groove 43 for the metal ring 52 is a groove concave inward from the outer surface of the rotating block 4. In the embodiment, the mounting groove 43 for the metal ring 52 is annular, and the metal ring 52 is correspondingly annular. After the metal ring 52 is inserted in the mounting groove 43 for the metal ring 52, at least one of the two ends of the metal ring 52 is fixed to the rotating block 4.

Different methods of fixing the ends of the metal ring 52 to the rotating block 4 can be adopted. For example, a fixed groove is further provided in the mounting groove 43 for the metal ring 52, the ends of the metal ring 52 are inserted in the fixed groove. In other embodiments, the ends of the metal ring 52 can be welded or riveted to the rotating block 4, which are all included in the protection scope of the present disclosure.

The rotating block 4 and the first cooperating member can cooperate with one or more of the components in the first embodiment. For example, the rotating block 4 and the elastic sheet 51 of the first embodiment shown in FIGS. 1-16 can be directly replaced with the rotating block 4 and the metal ring 52 of the second embodiment, to achieve a new structure of the rotating mechanism, which is also included in the protection scope of the present disclosure.

FIGS. 21-24 show the structure of the rotating block cooperating with the upper housing and the end cover. The difference between the third embodiment and the first embodiment is that, the structure of the rotating block 4 is different. Correspondingly, the structure of the end cover 6 and the structure of the accommodating cavity 71 of the upper housing 7 are changed accordingly to limit the movement space of the rotating block 4. In the embodiment, the rotating block 4 includes a second step portion 47 and a component mounting portion 45. The second step portion 47 is located above the component mounting portion 45. The first cooperating member is mounted on the outer surface of the component mounting portion 45. A diameter of the second step portion 47 is larger than a diameter of the component mounting portion 45. The second step portion 47 is used as the shaft cooperating portion cooperated with the rotating shaft 2. The structure can further increase the cooperation stability between the end cover 6 and the rotating block 4, enhance the limit function of the end cover 6 to the movement along the axial direction of the rotating block 4, and prevent the rotating block 4 from moving up and down.

In the third embodiment, the structure of the component mounting groove of the rotating block 4 and the first cooperating member can adopt the structure of the mounting groove 42 for the elastic sheet 51 on the rotating block 4 and the elastic sheet 51 in the first embodiment, or the structure of the metal ring 52 on the rotating block 4 and the mounting groove 43 for the metal ring 52. Furthermore, the structure can be combined with the other structures in the first embodiment. For example, the structure in the third embodiment can be combined with one or more components of the rotating shaft, the rotating knob, the plate-shaped base and the connecting component in the first embodiment shown in FIGS. 1-16, to get a new structure of the rotating mechanism, which is also included in the protection scope of the present disclosure.

In other embodiments of the present disclosure, other structures can be modified without departing from the protection scope of the present disclosure. For example, the housing of the rotating mechanism can be an integral housing instead of being divided to an upper housing and a lower housing. In another embodiment, the housing of the rotating mechanism can be divided to a left housing and a right housing. A semicircular accommodating cavity is formed on each of the left housing and the right housing. A circular accommodating cavity is formed when the left housing and the right housing are put together. For another example, the rotating shaft and the rotating block can be an integrally formed component, that is, the rotating component is an integrally formed component.

In the fourth embodiment, the fifth embodiment, and the sixth embodiment shown in FIGS. 25-37, the first cooperating member includes a recess, and the second cooperating member includes an elastic convex portion. When the rotating portion rotates relative to the housing until the convex portion faces the recess, the convex portion at least partially enters the recess. Therefore, the first cooperating member and the second cooperating member form elastic inserted cooperation. Here the elastic inserted cooperation in the embodiment means that when the convex portion at least partially enters the recess, and no external force is applied, the convex portion and the recess form relatively stable cooperation, to keep the rotating component at the current position. When an external force is applied to rotate the rotating component, the elastic deformation force of the convex portion is overcome, so as to separate the convex portion from the recess, then the rotating component can rotate relative to the housing.

FIGS. 25-34 show the structure of the rotating mechanism of the present disclosure according to the fourth embodiment. As shown in FIGS. 25-28, in the embodiment, the rotating mechanism includes a rotating component, a rotating rod 93 and a housing. Wherein, the rotating rod 93 cooperates with the rotating component, so that the rotation of the rotating component can move the rotating rod 93 along the axial direction of the stapler. The housing is provided with an accommodating cavity 71 for receiving the rotating component. At least one recess 49 is provided on the outer surface of the rotating component. The rotating mechanism further includes an elastic component 54 fixed in the accommodating cavity 71, and the elastic component 54 is located outside the rotating component. The elastic component 54 includes at least one convex portion 541 protruding toward the central axis of the rotating component. When the rotating portion rotates relative to the housing until the recess 49 faces the convex portion 541 of the elastic component 54, the convex portion 541 at least partially enters the recess 49.

Therefore, when the operator needs to rotate the stapler head, the operator needs to rotate the rotating component. In the initial state, the convex portion 541 of the elastic component 54 at least partially enters the recess 49, a resistance and a lagging will happen for the block function of the recess 49, to keep the convex portion 541 in the recess 49. Therefore, the rotating component is kept at its current position. When the operator further rotates the rotating component, the rotating force will overcome the elastic deformation force of the convex portion 541 to separate the convex portion 541 from the recess 49. Then the rotating component can be further rotated until the convex portion 541 of the elastic component 54 enters the next recess 49, and kept in the next recess 49. As the position of the recess 49 corresponds to the rotating angle of the stapler head, the rotating angle of the rotating component can be set by setting the position of the recess 49, and different rotating angles of the stapler head can be achieved. During operation, the convex portion 541 and the recess 49 can form relatively stable cooperation, so that the stapler head can be kept in a relatively stable state without manually external force, to prevent an uncontrollable rotation of the stapler head.

As shown in FIGS. 25-28, in the embodiment, the rotating component includes a rotating shaft 2 and a rotating block 4. The rotating shaft 2 cooperates with the rotating rod 93, so that when the rotating shaft 2 rotates, the rotating rod 93 is moved along the axial direction of the stapler. The rotating block 4 and the rotating shaft 2 are non-rotatably connected with each other. The recesses 49 are provided on the outer surface of the rotating block 4. The housing includes an upper housing 7 and a lower housing 8, the upper housing 7 is provided with the accommodating cavity 71.

Figure 27:
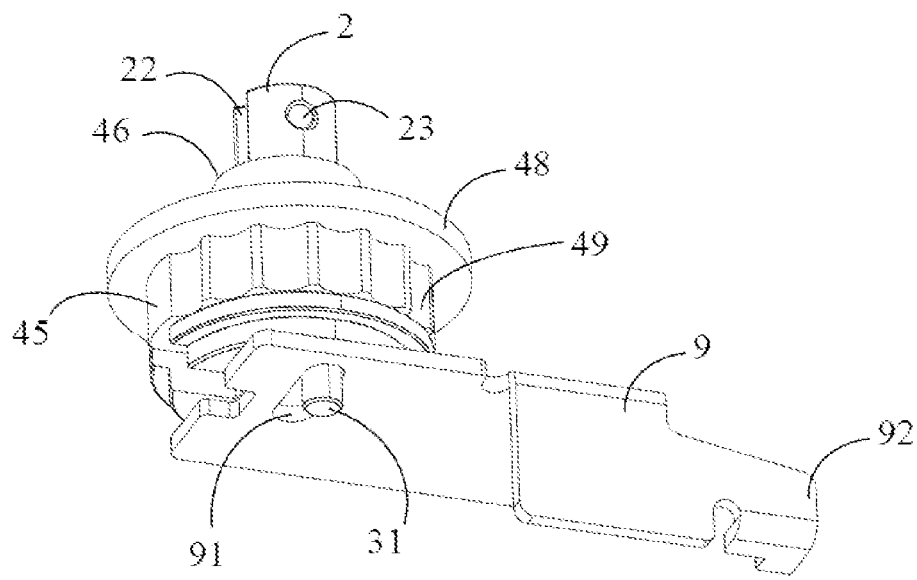
FIG. 27 is a structural schematic view showing a rotating component cooperating with a connecting component according to the fourth embodiment of the present disclosure.
Figure 28:
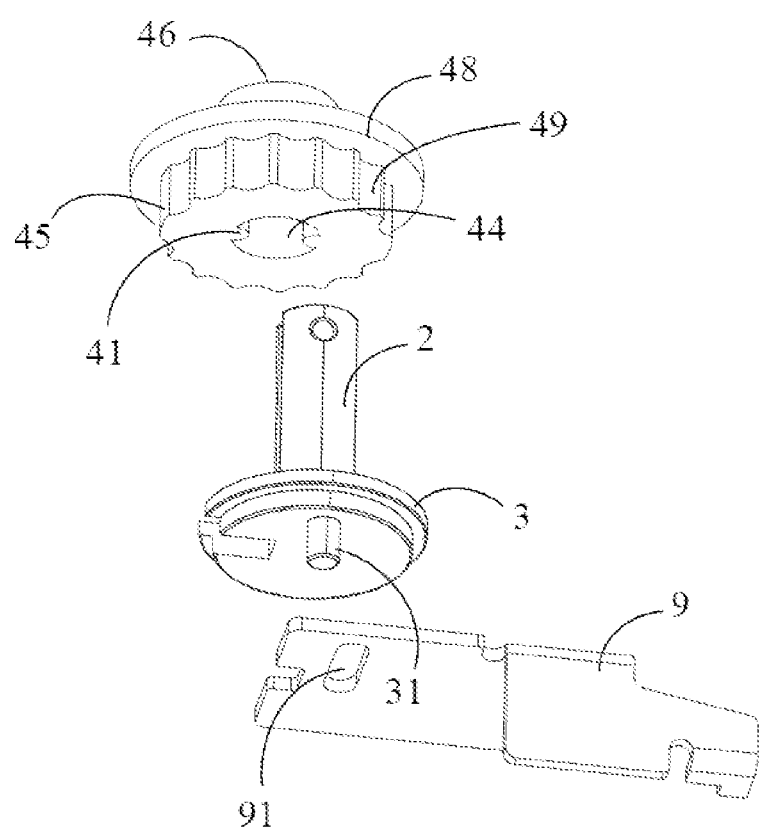
FIG. 28 is an exploded view of FIG. 7.

Furthermore, as shown in FIG. 27 and FIG. 28, a bottom portion, or the rotating shaft 2 is provided with a plate-shaped base 3, and the plate-shaped base 3 is under the rotating block 4. The plate-shaped base 3 and the rotating shaft 2 can be integrally formed, or the plate-shaped base 3 and the rotating shaft 2 can be two independent components fixed to each other. The outer surface of the rotating shaft 2 is provided with at least one first cooperating portion 22. A first through hole 44 is opened in the rotating block 4. The inner surface of the first through hole 44 is provided with at least one second cooperating portion 22. The rotating shaft 2 passes through the first through hole 44. The first cooperating portion 22 of the rotating shaft 2 is non-rotatably cooperated with the second cooperating portion 41 of the rotating block 4. In the embodiment, the first cooperating portion 22 is a groove located on an outer surface of the rotating shaft 2, the second cooperating portion 41 is a convex strip located on the inner surface of the first through hole 44. But the present disclosure is not limited to this. In other embodiments, the first cooperating portion can be a convex strip, the second cooperating portion can be a groove, or the first cooperating portion and the second cooperating portion are both strips or blocks. These embodiments are all included in the protection scope of the present disclosure.

The rotating mechanism further includes a connecting component 9, the plate-shaped base 3 is connected to the rotating rod 93 through the connecting component 9. The plate-shaped base 3 is eccentrically connected to the connecting component 9. Specifically, a bottom portion of the plate-shaped base 3 is provided with a convex shaft 31, and the connecting component 9 is provided with a waist-shaped cooperating hole 91. The convex shaft 31 passes through the cooperating hole 91. Preferably, the cooperating hole 91 is perpendicular to the axial direction of the stapler. In other alternative embodiments, a cooperating hole 91 can be provided on a bottom portion of the plate-shaped base 3, and a convex shaft passing through the cooperating hole is provided on the connecting component 9. When the rotating shaft 2 rotates, the plate-shaped base 3 is rotated, the connecting component 9 can be moved along the axial direction of the stapler by the eccentric cooperation between the plate-shaped base 3 and the connecting component 9, then the rotating rod 93 can be moved along the axial direction of the stapler.

Figure 25:
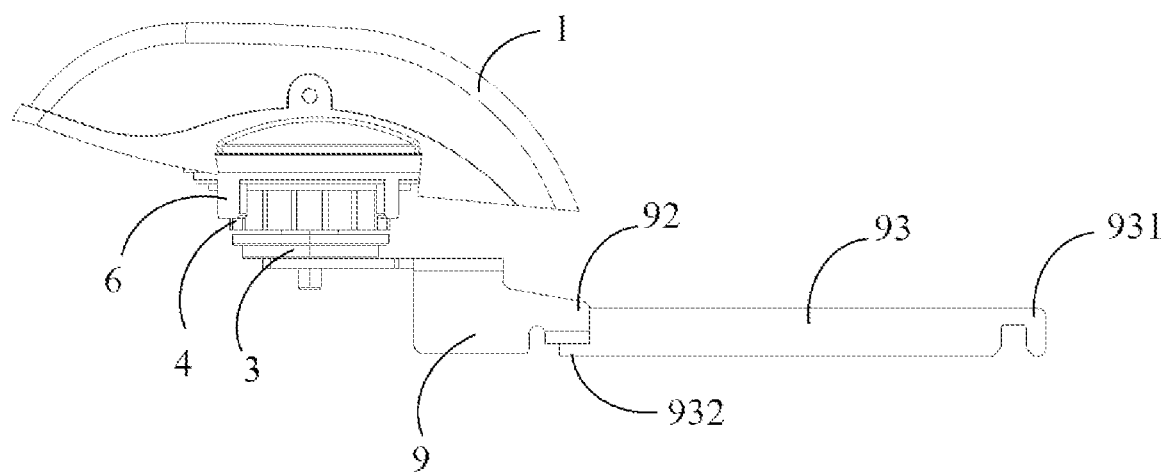
FIG. 25 is a structural schematic view of the rotating mechanism after the housing is removed according to a fourth embodiment of the present disclosure.
Figure 26:
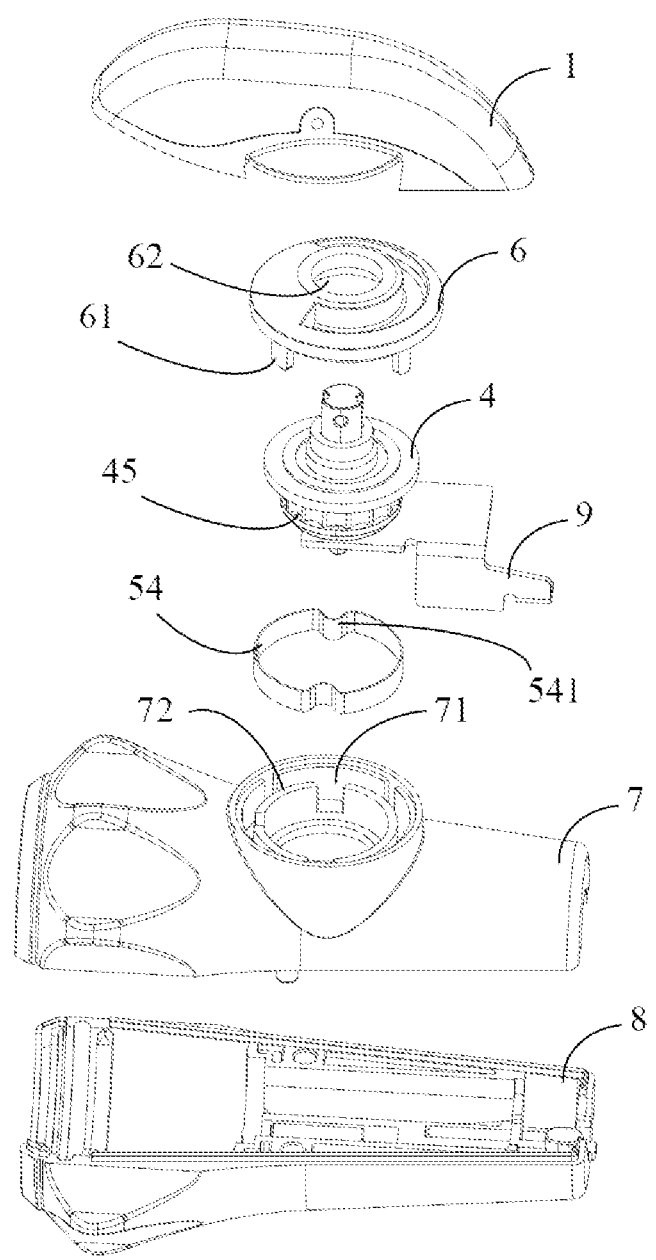
FIG. 26 is an exploded view of the rotating mechanism after the housing is removed according to the fourth embodiment of the present disclosure.

As shown in FIGS. 25-26, in the embodiment, the rotating mechanism includes a rotating knob 1. A pin hole 23 is provided on an upper portion of the rotating shaft 2. The rotating shaft 2 can be non-rotatably connected to the rotating knob 1 through a fixed pin passing through the pin hole 23. Therefore, when the rotating knob 1 rotates, the rotating shaft 2 is moved. When the doctor rotates the rotating knob 1, the rotating shaft 2 rotates the plate-shaped base 3, then the connecting component 9 is moved along the axial direction to move the rotating rod 93 along the axial direction. Then the stapler head can rotate clockwise or counterclockwise relative to the staple housing. The rotating mechanism further includes an end cover 6 located above the rotating block 4. The rotating shaft 2 passes through a second through hole 62 of the end cover 6. A bottom portion of the end cover 6 is provided with a plurality of limit columns 61. The upper housing 7 is further provided with a plurality of fixed grooves for the end cover 6. The limit columns 61 are inserted in the fixed grooves for the end cover 6. The end cover 6 can limit the axial position of the rotating block 4, to prevent the rotating block 4 from separating from the upper portion of the accommodating cavity 71 or moving up and down. The rotating block 4 is located in a space defined by the end cover 6 and the accommodating cavity 71. The rotating block 4 can only rotate relative to the upper housing 7, and cannot move along an axial direction of the rotating block 4.

As shown in FIGS. 26-28, in the embodiment, the rotating block 4 includes a first step portion 46 (that is, a shaft cooperating portion), a cover plate 48 and a component mounting portion 45. The outer surface of the component mounting portion 45 is provided with the recess 49. An outer diameter of the cover plate 48 is larger than an outer diameter of the component mounting portion 45, and the cover plate 48 covers the upper surface of the elastic component 54, to limit the movement of the elastic component 54 along the axial direction of the rotating component 4. Therefore, the elastic component 54 from dropping out of the upper housing 7 from the upper surface of the accommodating cavity 71 is prevented. Therefore, the elastic component 54 can be better kept in the space defined by the accommodating cavity 71 and the cover plate 48.

Figure 30:
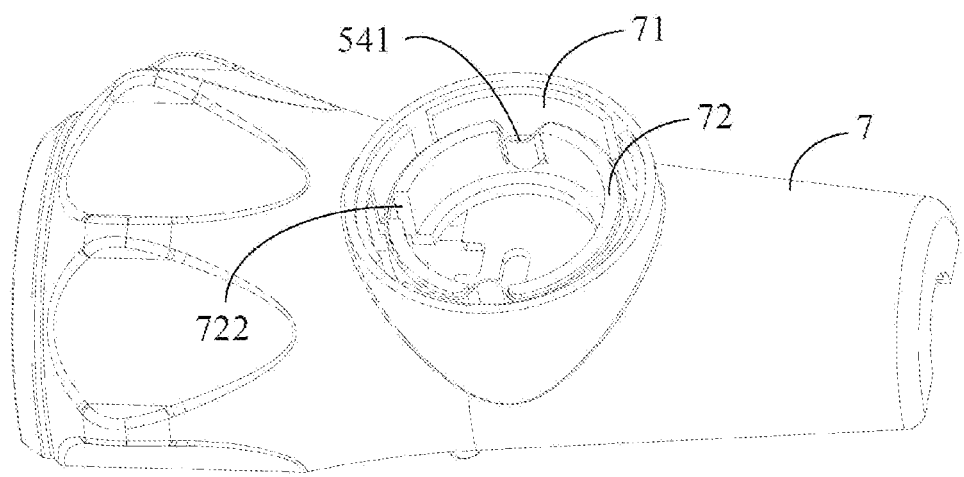
FIG. 30 is a structural schematic view of an upper housing according to the fourth embodiment of the present disclosure.
Figure 31:
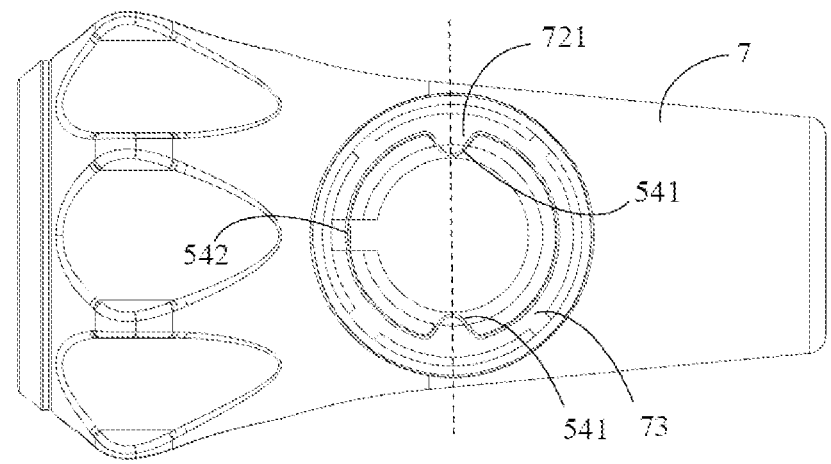
FIG. 31 is a top view of the upper housing according to the fourth embodiment of the present disclosure.
Figure 32:
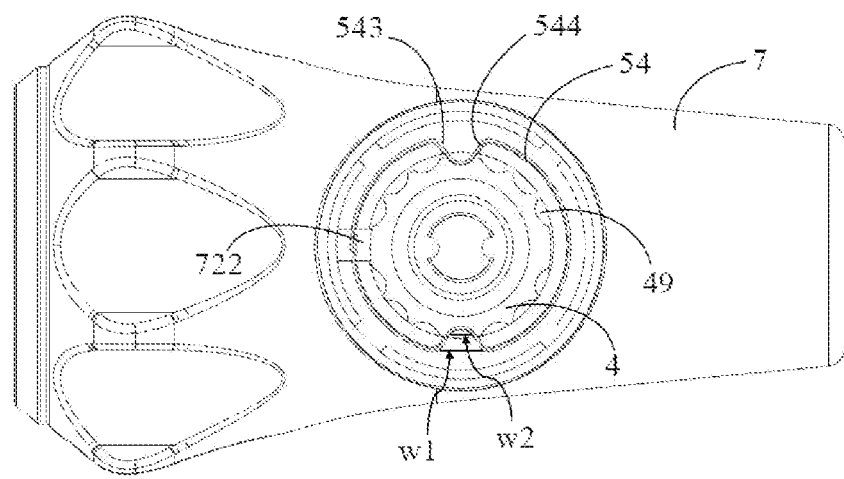
FIG. 32 is a structural schematic view showing the upper housing cooperating with the rotating block according to the fourth embodiment of the present disclosure.
Figure 33:
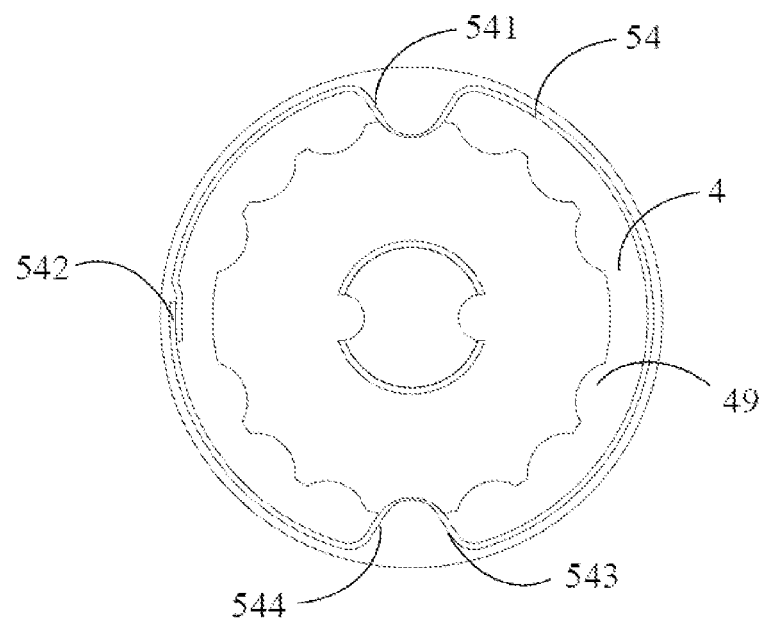
FIG. 33 is a bottom view showing the rotating block cooperating with the elastic sheets according to the fourth embodiment of the present disclosure.

As shown in FIGS. 30-32, in the embodiment, the elastic component 54 is annular. For example, the elastic component can use an elastic metal ring or other elastic annular structure. The accommodating cavity 71 is provided with a fixed component 72. The elastic component 54 surrounds outside the fixed component 72, and the inner wall of the elastic component 54 fits the outer wall of the fixed component 72, to effectively support the elastic component 54. As shown in FIG. 31, a gap 73 exists between the annular elastic component 54 and the inner wall of the accommodating cavity 71, so that when the convex portion 541 of the annular elastic component 54 is pressed by the rotating block 4 and deformed, an accommodating space for receiving the deformation of the convex portion 541 is big enough. The fixed component 72 is annular to adapt to the shape of the elastic component 54, and at least one opening 721 is provided at the position of the fixed component 72 corresponding to the elastic component 54. The convex portion 541 protrudes from the opening 721 toward the center of the accommodating cavity 71. With the cooperation between the convex portion 541 and the opening 721, the elastic sheet 54 won't rotate relative to the upper housing 7, to enhance the structural stability of the elastic component 54. The annular elastic component 54 can be formed by a strip-shaped elastic component 54. After the strip-shaped elastic component 54 surrounds outside the fixed component 72, two ends of the elastic component 54 are fixed through welding or other ways to form a connecting portion 542. The fixed component 72 is further provided with a mounting opening 722 facing the position of the connecting portion 542 of the two ends of the elastic component 54, to facilitate the mounting of the two ends of the elastic component 54 after the elastic component is fixed. The elastic component 54 can also be formed by bending the annular metal ring.

As shown in FIG. 32, to clearly show the cooperation between the recess 49 and the elastic component 54, the cover plate 48 is removed. The convex portion 541 includes an inclined first guiding surface 543 and an inclined second guiding surface 544. Therefore, a width w1 of one end of the convex portion 541 away from the rotating block 4 is larger than a width w2 of another end of the convex portion 513 close to the rotating block 4. In the embodiment, the end of the convex portion 541 away from the rotating block 4 is the end of the convex portion 541 away from the recess 49, the end of the convex portion 541 close to the rotating block 4 is the end of the convex portion 541 close to the recess 49. When the rotating block 4 rotates, the first guiding surface 543 and the second guiding surface 544 can better guide the convex portion 541 to enter or separate from the recess 49 of the rotating block 49. Preferably the first guiding surface 543 and the second guiding surface 544 are smooth surfaces, to make the rotating action smoother, and prevent an inconvenient operation caused by too big resistance.

Figure 29:
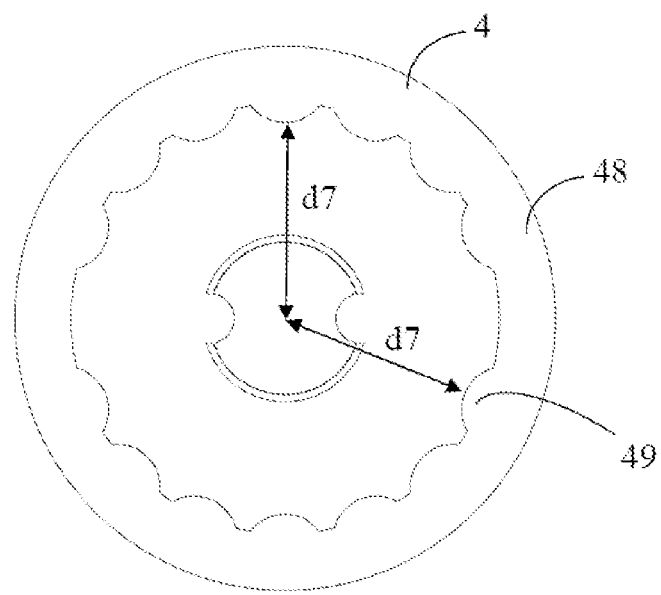
FIG. 29 is a bottom view of a rotating block according to the fourth embodiment of the present disclosure.
Figure 34:
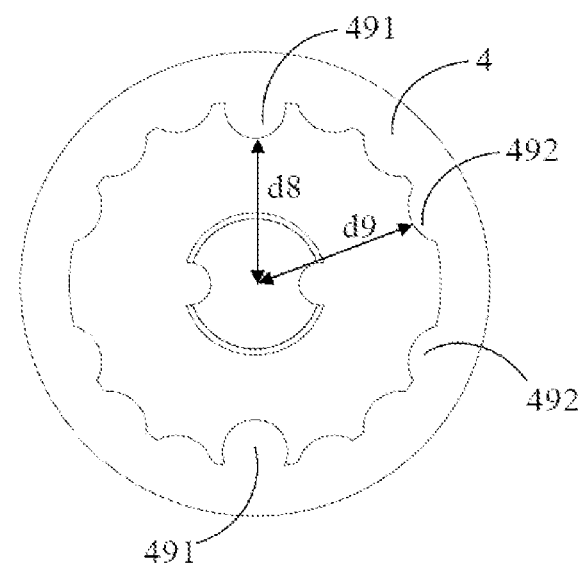
FIG. 34 is a bottom view of the rotating block having recesses with different depths according to the fourth embodiment of the present disclosure.

As shown in FIG. 29, in an embodiment, each of the plurality of recesses 49 has the same depth. That is, the distance between the bottom end of each recess 49 and the central axis of the rotating block 4 is d7. In another embodiment, as shown in FIG. 34, the recesses 49 can be divided into two kinds: at least one initial position recess 491 and at least one non-initial position recess 492. A depth of the initial position recess 491 is larger than a depth of the non-initial position recess 492. That is, a distance between a bottom end of the initial position recess 491 and the central axis of the rotating block 4 is d8, a distance between a bottom end of the non-initial position recess 492 and the central axis of the rotating block 4 is d9, and d8 is smaller than d9. There can be one or more initial position recess 491 and one or more non-initial position recess 492. When the stapler head is in its initial state, the convex portion 541 of the elastic component 54 is in the initial position recess 491. When the rotating block 4 rotates, the convex portion 541 of the elastic component 54 rotates and enters the non-initial position recess 492. The operator can sense the difference of the resistance to confirm the position of the initial position recess 491, and further precisely confirm the initial position of the stapler head, to realize a precise positioning of the initial position of the stapler head.

As shown in FIG. 31, in the embodiment, seen from the top view of the accommodating cavity 71, the central line of each convex portion 541 passes through the center of the accommodating cavity 71. But the present disclosure is not limited to this. In other alternative embodiments, none of the central lines of the convex portions 541 passes through the center of the accommodating cavity 71.

Figure 35:
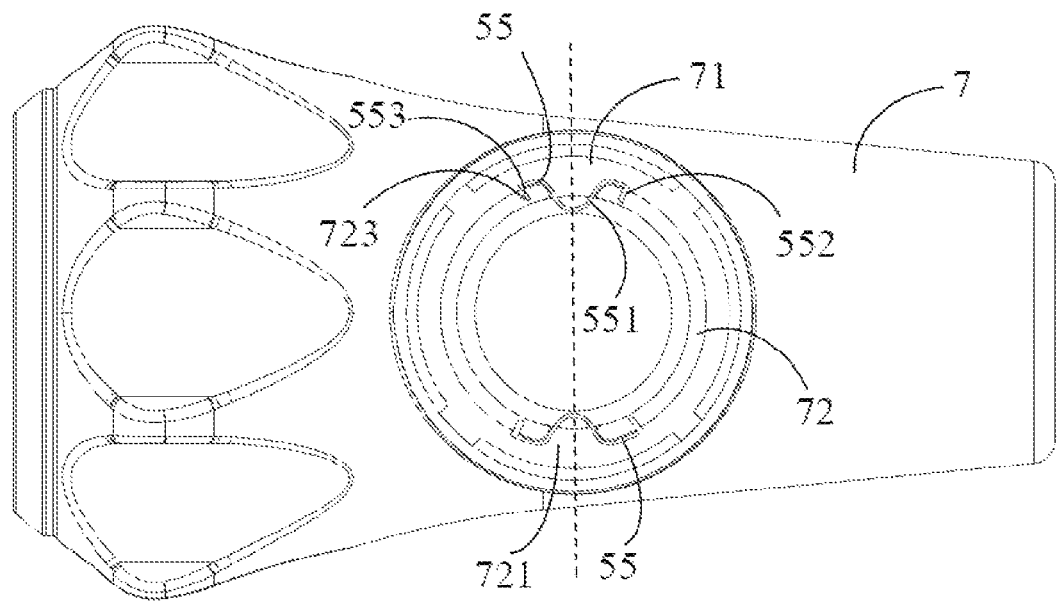
FIG. 35 is a top view of an upper housing according to a fifth embodiment of the present disclosure.
Figure 36:
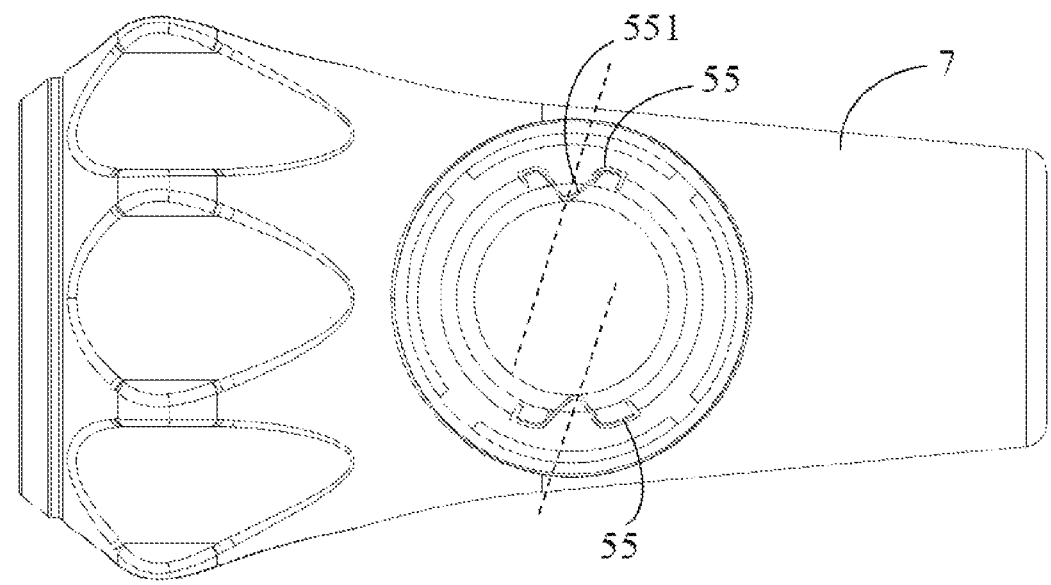
FIG. 36 is a top view of the upper housing using another kind of elastic sheet according to the fifth embodiment of the present disclosure.

FIG. 35 shows a rotating mechanism according to the fifth embodiment of the present disclosure. The difference between the fifth embodiment and the fourth embodiment is that the elastic component includes at least one elastic sheet 55. A convex portion 551 is formed between two ends of the elastic sheet 55. The first end 552 and the second end 553 of the elastic sheet 55 are fixed to the fixed component 72. The fixed component 72 is provided with a plurality of mounting grooves 723, the first end 552 and the second end 553 of the elastic sheet 55 are inserted in the mounting grooves 723. With the cooperation between the two ends of the elastic sheet 55 and the mounting grooves 723, the elastic sheet 55 is non-rotatably connected to the upper housing 7. The elastic sheet 55 can use an elastic metal sheet. The fixed component 72 can be annular and provided with a plurality of openings 721. The elastic sheet 55 cooperates with the openings 721 to prevent the elastic sheet 55 from rotating relative to the fixed component 72. In other alternative embodiments, the fixed component 72 can adopt other structures. For example, a fixed block is provided for each end of each elastic sheet 55, and the two ends of the elastic sheet 55 are inserted into the fixed blocks. In the embodiment, seen from the top view of the accommodating cavity 71, the central line of each convex portion 551 passes through the center of the accommodating cavity 71. FIG. 36 shows the elastic sheet 55 of another embodiment, wherein none of the central lines of the convex portions 551 passes through the center of the accommodating cavity 71.

Figure 37:
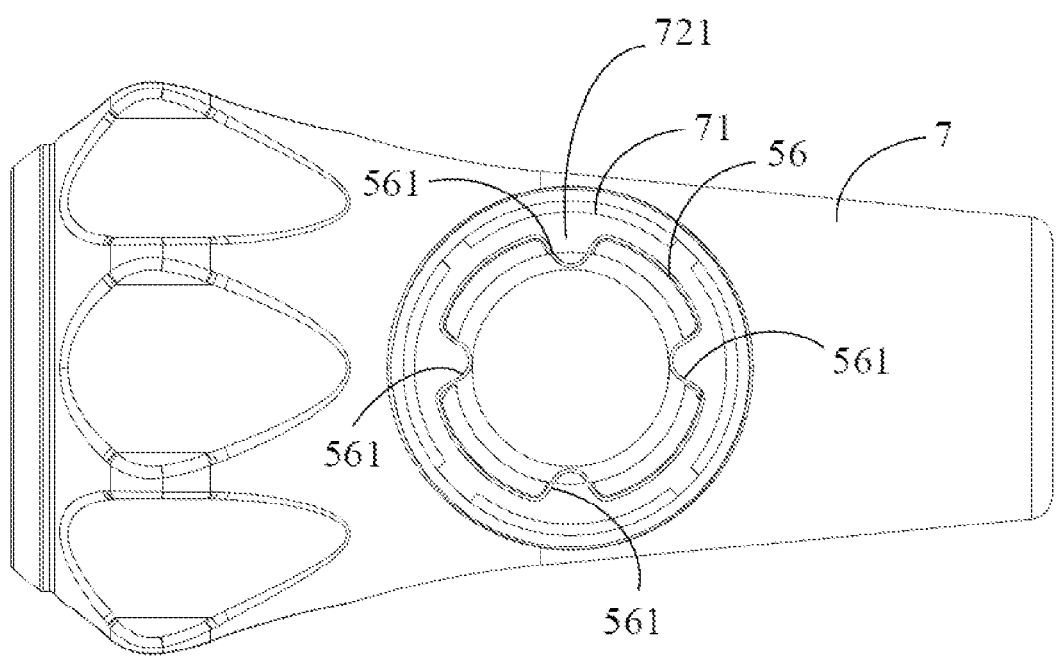
FIG. 37 is atop view of an upper housing according to a sixth embodiment of the present disclosure.

FIG. 37 shows a rotating mechanism according to the sixth embodiment of the present disclosure. The difference between the sixth embodiment and the fourth embodiment is that, the elastic component 56 is annular and has four convex portions 561. The elastic component 56 can be an elastic metal ring, sleeved outside the fixed component 72. With the cooperation between the convex portion 561 and the opening 721 of the fixed component 72, the elastic sheet 56 cannot be rotated relative to the upper housing 7. In other alternative embodiments, the number of the convex portions 561 on the elastic sheet 56 can be other numbers, and are not limited to the number shown in the figures.

The rotating mechanism and the surgical stapler of the present disclosure have the following advantages.

The present disclosure provides a rotating mechanism used for a surgical stapler, wherein, with the elastic inserted cooperation between the rotating component and the housing, the operator can set different rotating angles of the stapler head. The rotating angle of the stapler head can be precisely controlled by precisely controlling the axial moving distance of the rotating rod cooperating with the rotating component. Besides, when no external force is applied, the elastic inserted cooperation between the rotating component and the housing is relatively stable. Therefore, an uncontrollable rotation of the stapler head is prevented.

The above is a detailed description of the present disclosure in connection with the specific preferred embodiments, and the specific embodiments of the present disclosure are not limited to the description. Modifications and substitutions can be made without departing from the protection scope of the present disclosure.

What is claimed is:

1. A rotating mechanism used for a surgical stapler, wherein the rotating mechanism comprises:
   a rotating component, wherein an outer surface of the rotating component is provided with at least one first cooperating member;
   a rotating rod cooperated with the rotating component, so that the rotating rod is moved along an axial direction of the stapler when the rotating component rotates;
   a housing provided with an accommodating cavity for receiving the rotating component, wherein an inner side of the accommodating cavity is provided with at least one second cooperating member;
   wherein, the first cooperating member is elastic and includes an integrally-formed convex portion, the second cooperating member includes a recess, or, the first cooperating member includes a recess, the second cooperating member is elastic and includes an integrally-formed convex portion;
   wherein, when the rotating component rotates relative to the housing until the first cooperating member faces the second cooperating member, the first cooperating member and the second cooperating member form inserted cooperation;
   wherein, when the first cooperating member separates from the second cooperating member by an external force, the convex portion is deformed, and two ends of the convex portion respectively extend toward two sides.

2. The rotating mechanism of claim 1, wherein, the convex portion is arch-shaped, wherein when the first cooperating member separates from the second cooperating member by an external force, the height of the convex portion is decreased.

3. The rotating mechanism of claim 1, wherein, the first cooperating member includes the convex portion, the second cooperating member includes the recess; the outer surface of the rotating component is provided with at least one of elastic sheet, the convex portion is formed between two ends of the elastic sheet, the convex portion protrudes toward a direction away from the central axis of the rotating component, compared to the two ends of the elastic sheet.

4. The rotating mechanism of claim 3, wherein, the outer surface of the rotating component is provided with two mounting grooves corresponding to the two ends of each elastic sheet, the two ends of the elastic sheet are mounted in the corresponding mounting grooves.

5. The rotating mechanism of claim 4, wherein, each of the mounting grooves includes at least one extension section and at least one inclined section connected to a first end of the extension section, an angle forms between the inclined section and the extension section, and the extension section is connected to the outer surface of the rotating component; at least one end of the elastic sheet is located in the extension section, and the convex portion of the elastic sheet partially enters the inclined section.

6. The rotating mechanism of claim 5, wherein, the mounting groove corresponding to at least one end of the elastic sheet further includes at least one fixed section connected to a second end of the extension section, an angle forms between the fixed section and the extension section, and the fixed section receives one end of the elastic sheet.

7. The rotating mechanism of claim 1, wherein, the first cooperating component includes the elastic convex portion, the second cooperating member includes the recess; at least one metal ring is sleeved on the outer surface of the rotating component, and the at least one convex portion is formed on the metal ring.

8. The rotating mechanism of claim 7, wherein, a part of the outer surface of the rotating component is concave inward to form a mounting groove, and the metal ring is inserted in the mounting groove.

9. The rotating mechanism of claim 1, wherein, the first cooperating member includes the recess, the second cooperating member includes the convex portion, the inner side of the accommodation cavity is provided with a fixed component and an annular elastic component surrounding the fixed component, the at least one convex portion is formed on the annular elastic component.

10. The rotating mechanism of claim 9, wherein, the fixed component is annular to be adapted to the shape of the annular elastic component, and an opening is provided at a position corresponding to each convex portion on the fixed component.

11. The rotating mechanism of claim 9, wherein, a gap is formed between the annular elastic component and the inner wall of the accommodating cavity.

12. The rotating mechanism of claim 1, wherein, the first cooperating member includes the recess, the second cooperating member includes the convex portion; the inner side of the accommodating cavity is provided with a fixed component and at least one elastic sheet fixed to the fixed component, the convex portion is formed between two ends of the elastic sheet.

13. The rotating mechanism of claim 1, wherein, the first cooperating member includes the convex portion, seen from the top view of the rotating component, a central line of each convex portion passes a center of the rotating component or doesn't pass a center of the rotating component;
or, the second cooperating member includes the convex portion, seen from the top view of the accommodating cavity, a central line of each convex portion passes a center of the accommodating cavity or doesn't pass a center of the accommodating cavity.

14. The rotating mechanism of claim 1, wherein, the convex portion includes an inclined first guiding surface and an inclined second guiding surface, so that a width of one end of the convex portion facing toward the recess is less than a width of another end of the convex portion away from the recess.

15. The rotating mechanism of claim 1, wherein, there are a plurality of recesses including at least one initial position recess and at least one non-initial position recess, a depth of the initial position recess is larger than a depth of the non-initial position recess.

16. The rotating mechanism of claim 1, wherein, the rotating component includes:
a rotating shaft cooperated with the rotating rod, so that the rotating rod is moved along an axial direction of the stapler when the rotating shaft rotates;
a rotating block cooperated with the rotating shaft, so that the rotating block is rotated when the rotating shaft rotates, wherein an outer surface of the rotating block is provided with the at least one first cooperating member.

17. The rotating mechanism of claim 16, wherein, an outer surface of the rotating shaft is provided with at least one first cooperating portion, a first through hole is provided in the rotating block, and an inner side of the first through hole is provided with at least one second cooperating portion, the rotating shaft passes through the first through hole, and the first cooperating portion of the rotating shaft non-rotatably cooperates with the second cooperating portion of the rotating block.

18. The rotating mechanism of claim 17, wherein, the rotating block includes a shaft cooperating portion and a component mounting portion, the shaft cooperating portion is located above the component mounting portion, the first cooperating member is provided on an outer surface of the component mounting component, a diameter of the shaft cooperating portion is larger than or smaller than a diameter of the component mounting portion.

19. The rotating mechanism of claim 18, wherein, the first cooperating member includes the convex portion, the second cooperating member includes the recess, an outer diameter of the component mounting portion at a position corresponding to the first cooperating member is smaller than an outer diameter of the component mounting portion at other positions.

20. A surgical stapler comprising the rotating mechanism according to claim 1.

* * * * *

UNITED STATES PATENT AND TRADEMARK OFFICE
CERTIFICATE OF CORRECTION

PATENT NO. : 12,048,432 B2
APPLICATION NO. : 17/756394
DATED : July 30, 2024
INVENTOR(S) : Zhi Chen et al.

It is certified that error appears in the above-identified patent and that said Letters Patent is hereby corrected as shown below:

On the Title Page

Item (30), reads as:
Nov. 28, 2019 (CN) .......................... 201911195242.X
Nov. 28, 2019 (CN) .......................... 201922094449.X
Apr. 13, 2020 (CN) .......................... 202020538343.X Should read as follows:
Nov. 28, 2019 (CN) .......................... 201911195242
Nov. 28, 2019 (CN) .......................... 201922094449
Apr. 13, 2020 (CN) .......................... 202020538343

Signed and Sealed this
Twenty-second Day of October, 2024

Katherine Kelly Vidal
*Director of the United States Patent and Trademark Office*